United States Patent
Black et al.

(10) Patent No.: US 10,463,501 B2
(45) Date of Patent: Nov. 5, 2019

(54) EXPANDABLE SPINAL CAGES

(71) Applicant: DeGen Medical, Inc., Florence, SC (US)

(72) Inventors: Craig Black, Florence, SC (US); Kidong Yu, Florence, SC (US)

(73) Assignee: DeGen Medical, Inc., Florence, SC (US)

( * ) Notice: Subject to any disclaimer, the term of this patent is extended or adjusted under 35 U.S.C. 154(b) by 558 days.

(21) Appl. No.: 15/137,500

(22) Filed: Apr. 25, 2016

(65) Prior Publication Data
US 2017/0304071 A1   Oct. 26, 2017

(51) Int. Cl.
*A61F 2/44* (2006.01)
*A61F 2/30* (2006.01)

(52) U.S. Cl.
CPC ............ *A61F 2/4425* (2013.01); *A61F 2/447* (2013.01); *A61F 2/4455* (2013.01); *A61F 2002/30471* (2013.01); *A61F 2002/30507* (2013.01); *A61F 2002/30538* (2013.01); *A61F 2002/30556* (2013.01)

(58) Field of Classification Search
CPC ........................................................ A61F 2/44
See application file for complete search history.

(56) References Cited

U.S. PATENT DOCUMENTS

| | | |
|---|---|---|
| 5,653,763 A | 8/1997 | Errico et al. |
| 6,129,763 A | 10/2000 | Chauvin et al. |
| 6,176,882 B1 | 1/2001 | Biedermann et al. |
| 6,375,682 B1 | 4/2002 | Fleischmann et al. |
| 6,443,989 B1 | 9/2002 | Jackson |
| 6,491,724 B1 | 12/2002 | Ferree |
| 6,562,074 B2 | 5/2003 | Gerbec et al. |
| 6,685,742 B1 | 2/2004 | Jackson |
| 7,018,415 B1 | 3/2006 | McKay |
| 7,094,257 B2 | 8/2006 | Mujwid et al. |
| 7,708,779 B2 | 5/2010 | Edie et al. |
| 7,875,078 B2 | 1/2011 | Wysocki et al. |
| 8,057,548 B2 | 11/2011 | Abernathie et al. |
| 8,062,375 B2 | 11/2011 | Glerum et al. |
| 8,267,939 B2 | 9/2012 | Cipoletti et al. |
| 8,696,751 B2 | 4/2014 | Ashley et al. |
| 2010/0286779 A1 | 11/2010 | Thiobodeau |

(Continued)

FOREIGN PATENT DOCUMENTS

WO     WO2015198335     12/2015

OTHER PUBLICATIONS

International Searching Authority, "Notification of Transmittal of the International Search and the Written Opinion of the International Search Authority, or the Declaration" for application No. PCT/US2017/029092, dated Jul. 24, 2017, pp. 1-12.

(Continued)

*Primary Examiner* — David W Bates
(74) *Attorney, Agent, or Firm* — Buchanan Van Tuinen LLC

(57) ABSTRACT

The technical description relates to expandable spinal cages. An example expandable spinal cage is configured to engage a vertebra. An example expandable spinal cage includes a fixed member a lifting member, a driving member, and a locking member. An example expandable spinal cage has a first configuration and a second configuration.

20 Claims, 11 Drawing Sheets

(56) References Cited

U.S. PATENT DOCUMENTS

| | | |
|---|---|---|
| 2013/0158669 A1 | 6/2013 | Sungarian et al. |
| 2015/0272743 A1 | 10/2015 | Jimenez et al. |
| 2015/0342749 A1 | 12/2015 | Baynham |
| 2017/0156885 A1* | 6/2017 | Zur ...................... A61F 2/4425 |

OTHER PUBLICATIONS

International Bureau. "International Preliminary Report on Patentability" for application No. PCT/2017/029092, dated Oct. 30, 2018, pp. 1-6.

* cited by examiner

EXPANDABLE SPINAL CAGES

FIELD

The disclosure relates to the field of implantable medical devices. More particularly, the disclosure relates to medical devices suitable for implantation in spaces between bones, such as the spaces between vertebral bodies in a spinal column of a vertebrate. Specific examples relate to the field of expandable spinal cages disposed between adjacent vertebrae of a spinal column.

BACKGROUND

Over time, bone may degenerate as a result of trauma, disease, and natural processes, such as aging. Bone degeneration can affect surrounding tissues and have significant negative impact on the lifestyle of an animal. For example, destabilization of a spine in a vertebrate, such as a human being, may result in alteration of the spacing between adjacent vertebrae. This can place pressure on nerves that pass between the vertebral bodies. In turn, this pressure can cause pain, discomfort, and, eventually, nerve damage.

One way to alleviate the pain and discomfort that occurs after the degeneration or destabilization of a portion of the spine is to implant a medical device into the space between two adjacent vertebrae. Implanted in this manner, the medical device supports the structure of the spine by maintaining a desired spacing and angular positioning between the adjacent vertebrae.

The art includes several examples of devices useful for modifying the angular positioning between two adjacent vertebrae. One such device, described in U.S. Pat. No. 8,062,375 to Glerum, et al., for EXPANDABLE FUSION DEVICE AND METHOD OF INSTALLATION THEREOF, includes an expandable fusion device having a first endplate and a second endplate. When the device is transitioned between a first configuration and a second configuration, each of the first and second endplates extends away from the longitudinal axis of the device and places force on a vertebra in order to modify the spacing between the vertebrae.

Despite this and other examples, a need exists for improved expandable spinal cages.

BRIEF SUMMARY OF SELECTED EXAMPLES

Various example expandable spinal cages are described and illustrated herein.

An example expandable spinal cage having a first configuration and a second configuration and configured to engage a vertebra comprises a fixed member having a proximal end, a distal end, a base, an open end substantially opposite the base, an inner surface, and an outer surface, the base, the open end, and the inner surface cooperatively defining a cavity, the inner surface and the outer surface cooperatively defining a passageway on the proximal end in fluid communication with the cavity, a lifting member partially disposed within the cavity of the fixed member and comprising a contacting member and a transition member, the contacting member having a lower surface and an upper surface configured to contact the vertebra, the contacting member being disposed adjacent the open end, the transition member in contact with the lower surface, a driving member disposed within the cavity of the fixed member and configured to exert force on the lifting member, and a locking member configured to be inserted into the passageway and contact the driving member to transition the expandable spinal cage from the first configuration to the second configuration, the upper surface is disposed further from the base when the expandable spinal cage is in the second configuration than when the expandable spinal cage is in the first configuration.

Another example expandable spinal cage having a first configuration and a second configuration and configured to engage a vertebra comprises a fixed member having a proximal end, a distal end, a first lateral side, a second lateral side substantially opposite the first lateral side, a base, an open end substantially opposite the base, an inner surface, and an outer surface, the base, the open end, and the inner surface cooperatively defining a cavity, the inner surface and the outer surface cooperatively defining a first passageway on the proximal end in fluid communication with the cavity, the first lateral side defining an inner surface and an outer surface, the second lateral side defining an inner surface and an outer surface, the first lateral side inner surface defining a first slot, the second lateral side inner surface defining a second slot, the fixed member defining a second passageway extending from the inner surface of the first lateral side to the outer surface of the first lateral side, and a third passageway extending from the inner surface of the second lateral side to the outer surface of the second lateral side, a lifting member partially disposed within the cavity of the fixed member and comprising a contacting member and a transition member, the contacting member having a lower surface and an upper surface configured to contact the vertebra, the contacting member being disposed adjacent the open end, the transition member in contact with the lower surface, the transition member defining a first stabilizing mechanism configured to engage the first slot, the transition member defining a second stabilizing mechanism configured to engage the second slot, a driving member disposed within the cavity of the fixed member and configured to exert force on the lifting member, and a locking member configured to be inserted into the first passageway and contact the driving member to transition the expandable spinal cage from the first configuration to the second configuration, the upper surface is disposed further from the base when the expandable spinal cage is in the second configuration than when the expandable spinal cage is in the first configuration.

Another example expandable spinal cage having a first configuration and a second configuration and configured to engage a vertebra comprises a fixed member having a proximal end, a distal end, a first lateral side, a second lateral side substantially opposite the first lateral side, a base, an open end substantially opposite the base, an inner surface, and an outer surface, the base, the open end, and the inner surface cooperatively defining a cavity, the inner surface and the outer surface cooperatively defining a passageway on the proximal end in fluid communication with the cavity, the first lateral side defining a first lateral side inner surface, the second lateral side defining a second lateral side inner surface, the first lateral side inner surface defining a first slot, the second lateral side inner surface defining a second slot, a lifting member partially disposed within the cavity of the fixed member and comprising a contacting member, a transition member, a connecting member, and a hinge member, the contacting member having a lower surface and an upper surface configured to contact the vertebra, the contacting member being disposed adjacent the open end, the transition member in contact with the lower surface, the transition member defining a first stabilizing mechanism configured to engage the first slot, the transition member defining a second stabilizing mechanism configured to engage the second slot, a driving member disposed within the cavity of the fixed member and configured to exert force on the lifting member, and a locking member configured to be inserted into the passageway and contact the driving member to transition the expandable spinal cage from the first configuration to the second configuration, the upper surface is disposed further from the base when the expandable spinal cage is in the second configuration than when the expandable spinal cage is in the first configuration, the upper surface is disposed on a plane that is set at a first, non-orthogonal angle to a plane on which the base is disposed when the expandable spinal cage is in the second configuration, and the first, non-orthogonal angle is between about 1° and about 30°.

Additional understanding of claimed expandable spinal cages can be obtained by reviewing the detailed description of selected examples, below, with reference to the appended drawings.

DETAILED DESCRIPTION OF SELECTED EXAMPLES

Figure 1:
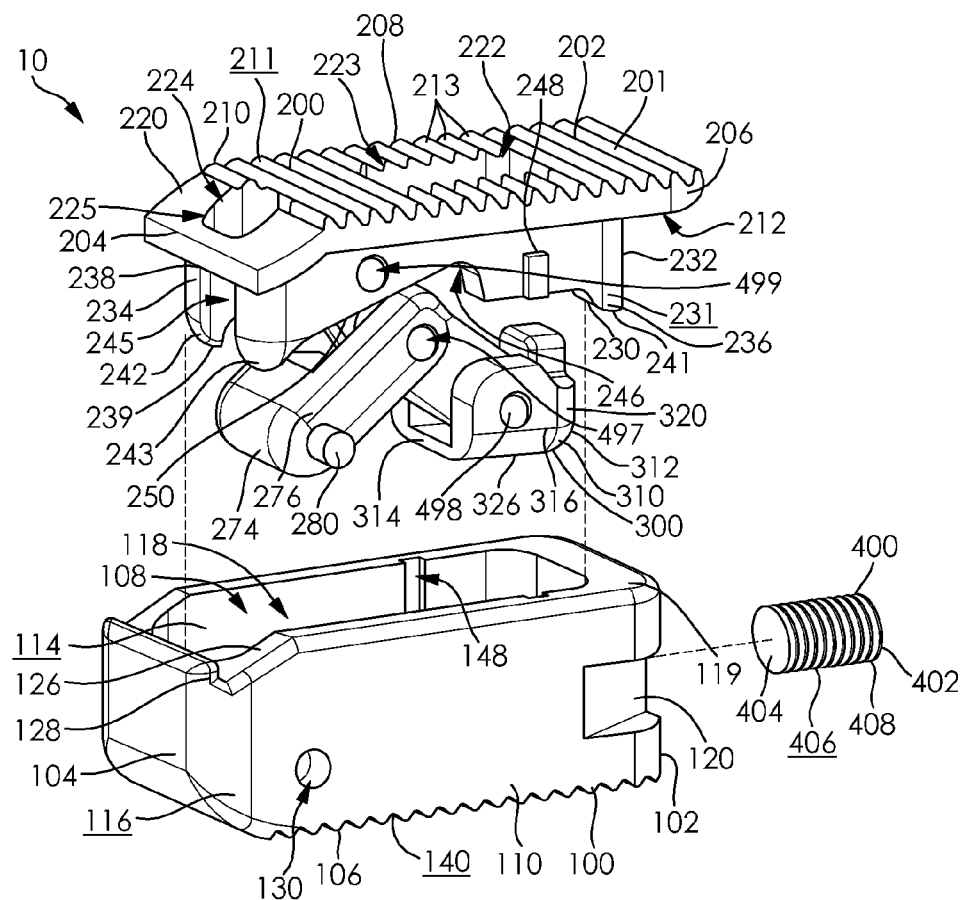
FIG. 1 is an exploded view of a first example expandable spinal cage.
Figure 2:
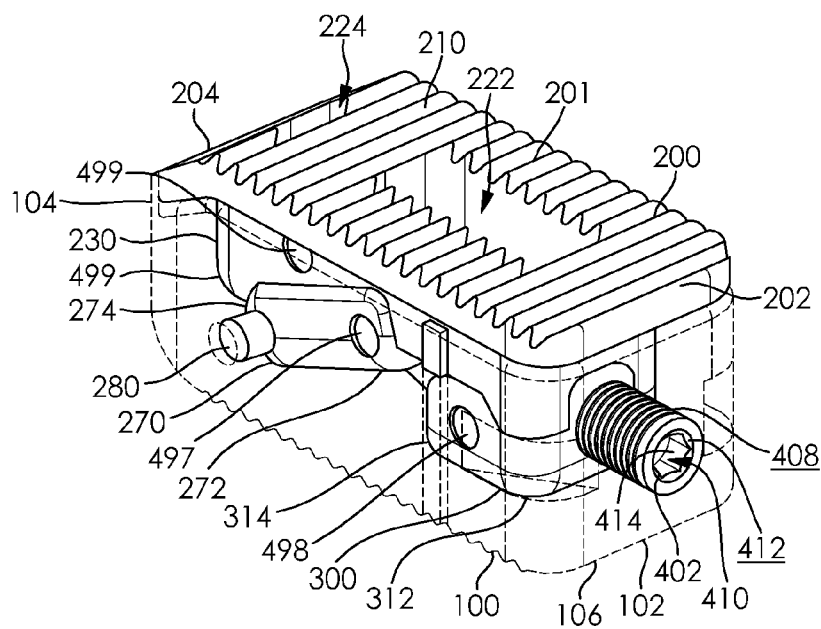
FIG. 2 is a perspective view of the expandable spinal cage illustrated in FIG. 1, with the fixed member illustrated in phantom. The expandable spinal cage is illustrated in a first configuration.
Figure 3:
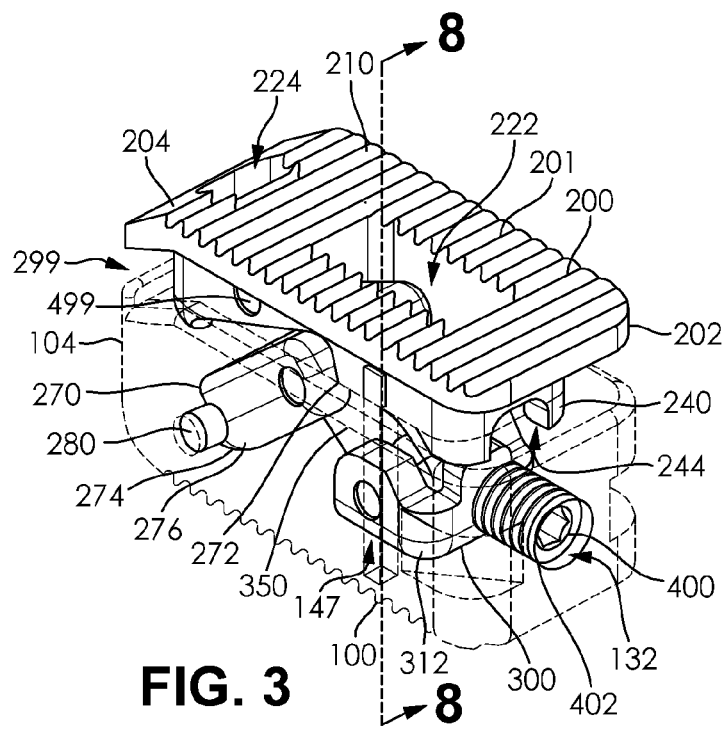
FIG. 3 is a perspective view of the expandable spinal cage illustrated in FIG. 1, with the fixed member illustrated in phantom. The expandable spinal cage is illustrated in a second configuration.
Figure 4:
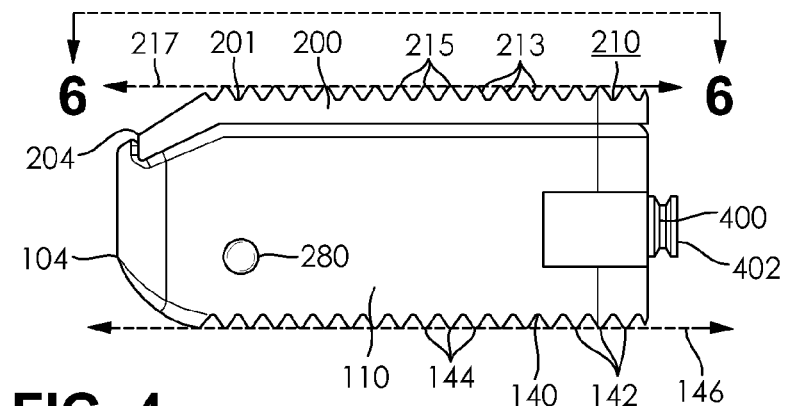
FIG. 4 is a side view of the expandable spinal cage illustrated in FIG. 1. The expandable spinal cage is illustrated in a first configuration.
Figure 5:
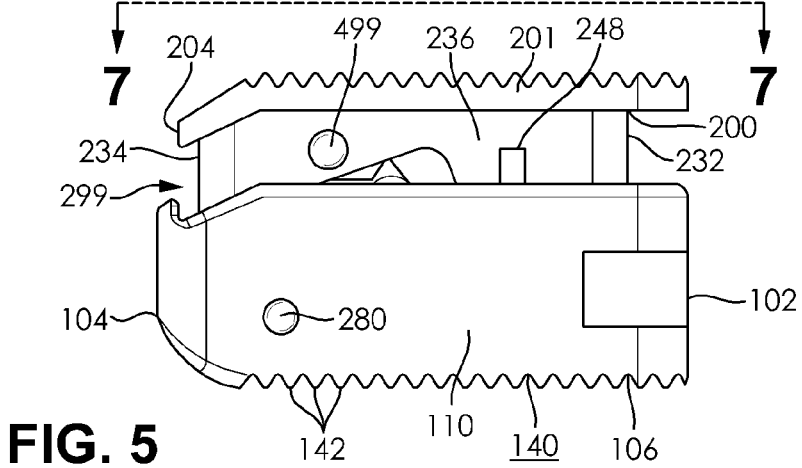
FIG. 5 is a side view of the expandable spinal cage illustrated in FIG. 1. The expandable spinal cage is illustrated in a second configuration.

The following detailed description and the appended drawings describe and illustrate various example expandable spinal cages. The description and illustration of these examples are provided to enable one skilled in the art to make and use expandable spinal cages. They are not intended to limit the scope of the claims in any manner.

The medical devices described herein may be implanted within the spinal column of an animal, such as a human, to assist in maintaining support within the spinal column. The example expandable spinal cages described below are suitable for use within various intervertebral spaces along a spinal column. The expandable spinal cages are configured to be disposed between adjacent vertebrae of a spinal column.

Each of FIGS. 1, 2, 3, 4, 5, 6, 7, 8, 8A, 9, 10, and 11 illustrates an example expandable spinal cage 10 or one or more components thereof. The expandable spinal cage 10 comprises a fixed member 100, a lifting member 200, a driving member 300, a locking member 400, and pins 497, 498, 499. The expandable spinal cage 10 has a first configuration and a second configuration.

The fixed member 100 has a proximal end 102, a distal end 104, a base 106, an open end 108 substantially opposite the base 106, a first lateral side 110, a second lateral side 112, an inner surface 114, and an outer surface 116. The base 106, the open end 108, and the inner surface 114 cooperatively define a cavity 118.

The proximal end 102, first lateral side 110, and outer surface 116 cooperatively define a first notch 120. The proximal end 102, second lateral side 112, and outer surface 116 also cooperatively define a second notch (not illustrated in the Figures). Each of the first notch 120 and the second notch is configured to allow the fixed member 100 to be grasped by a medical device or instrument (not illustrated in the Figures), such as a tool used during implantation of the expandable spinal cage 10. The medical device or instrument may be used to insert the expandable spinal cage 10 within a vertebral column. Various notches may be defined by any portion of the fixed member in other embodiments. A skilled artisan will be able to determine how to suitably configure the notches, if desired, according to a particular example based on various considerations, including the nature and configuration of any tool or instrument intended to be used with the spinal cage, such as during implantation. In other example embodiments, one or more notches may be fully or partially defined by any portion of the fixed member, including one or more of the base, the proximal end, the distal end, the first lateral side, and the second lateral side. In example embodiments, the fixed member may define zero, one, two, three, or more than three notches. In other example embodiments, one or more mechanical connectors of any type and/or one or more adhesives may be used as an alternative to notches.

The first lateral side 110, inner surface 114, and outer surface 116 cooperatively define a first pin passageway 130 extending from the outer surface 116 to the inner surface 114. The second lateral side 112, inner surface 114, and outer surface 116 cooperatively define a second pin passageway (not illustrated in the Figures) extending from the outer surface 116 to the inner surface 114. Each of the first 130 and second pin passageways is substantially cylindrical in shape and is configured to at least partially house a pin, such as pin 400. Any portion of the fixed member may define the first and second pin passageways, however. They may also have any suitable size, shape, and configuration. A skilled artisan will be able to determine how to suitably form the first and second pin passageways according to a particular example based on various considerations, including the size, shape, and configuration of the pin and lifting member in a spinal cage according to a particular example. In example embodiments, the first and second pin passageways may have any shape, including pill, pyramid, box, and cone. Also in example embodiments, the first and second pin passageways may be defined by any portion of the fixed member, including one or more of the first lateral side, second lateral side, proximal end, distal end, and base.

The proximal end 102, inner surface 114, and outer surface 116 cooperatively define a locking member passageway 132 extending from the outer surface 116 to the inner surface 114. The locking member passageway 132 is substantially cylindrical in shape and is configured to at least partially house a locking member, such as locking member 400. The locking member passageway 132 includes an inner surface 134 defining a threaded portion 136. Any portion of the fixed member may define the locking member passageway, however. The locking member passageway may also have any shape, size, and configuration. A skilled artisan will be able to determine how to suitably form the locking member passageway, if desired, according to a particular example based on various considerations, including the size, shape, and configurations of the driving member and lifting member. In example embodiments, the locking member passageway may have any shape, including pill, pyramid, box, and cone. Also in example embodiments, the locking member passageway may be defined by any portion of the fixed member, including one or more of the first lateral side, second lateral side, proximal end, distal end, and base.

The open end 108 is at least partially defined by each of the inner surface 114, the proximal end 102, the distal end 104, the first lateral side 110, and the second lateral side 112. These portions of the fixed member 100 cooperatively form a perimeter 119 adjacent the open end 108. The perimeter 119 is substantially rounded rectangular in shape and includes a depressed portion 126 cooperatively defined by the distal end 104, the first lateral side 110, and the second lateral side 112. The depressed portion 126 is disposed adjacent a ridge 128 that is defined by the distal end 104; it is disposed between the ridge 128 and the non-depressed portion of the perimeter 119. The depressed portion 126 extends toward the base 106, while the ridge 128 extends substantially perpendicular relative to the plane (described below) on which the base 106 is disposed. The fixed member may define any perimeter, however, and the perimeter may have any size, shape, and configuration. A skilled artisan will be able to determine a suitable perimeter according to a particular example based on various considerations, including the size, shape, and configuration of the lifting member. In example embodiments, the perimeter may have any shape, including circular, rectangular, triangular, elliptical, oval, and pentagonal. In example embodiments, the perimeter may not define one or both of the depressed portion and the ridge. In example embodiments, the depressed portion may be disposed away from, parallel to, or substantially parallel to the base and contain no ridge.

The base 106 defines a lower surface 140. The lower surface 140 includes of a set of protruding ridges 142 configured to engage a vertebra. Each protruding ridge of the set of protruding ridges 142 defines a tip 144. Each of the tips 144 defined by the protruding ridges of the set of protruding ridges 142 is disposed on a first plane 146. Each protruding ridge is substantially the same size and shape as each other protruding ridge of the set of protruding ridges 142. A skilled artisan will be able to determine how to suitably configure the protruding ridges according to a particular example based on various considerations, including the vertebra that the protruding ridges will engage and the desirability of including bone-engaging ridges. In example embodiments, any suitable mechanical connector and/or one or more adhesive may be used as an alternative to protruding ridges to engage a vertebra. In other example embodiments, the lower surface of the base may not include any mechanism for engaging a vertebra. In example embodiments, the lower surface may define a pattern configured to engage in assisting a vertebra; such patterns may include three-dimensional (3D) printed patterns, serrated patterns, and other suitable patterns.

The lifting member 200 includes a contacting member 201, a transition member 230, a connecting member 250, and a hinge member 270. The lifting member 200 is at least partially disposed within the cavity 118 defined by the fixed member 100.

The contacting member 201 includes a proximal end 202, a distal end 204, a first lateral side 206, a second lateral side 208, a top 210, and a bottom 212.

The top 210 defines an upper surface 211. The upper surface 210 includes of a set of protruding ridges 213 configured to engage a vertebra. Each protruding ridge of the set of protruding ridges 213 defines a tip 215. Each of the tips 215 defined by the protruding ridges of the set of protruding ridges 215 is disposed on a first plane 217. Each protruding ridge is substantially the same size and shape as each other protruding ridge of the set of protruding ridges 213. A skilled artisan will be able to determine how to suitably configure the protruding ridges according to a particular example based on various considerations, including the size, shape, and configuration of the vertebra that the protruding ridges will engage and the desirability of including bone-engaging ridges. In example embodiments, any suitable mechanical connector and/or one or more adhesive may be used as an alternative to protruding ridges to engage a vertebra. In other example embodiments, the top may not include any mechanism for engaging a vertebra. In example embodiments, the upper surface may define a pattern configured to engage in assisting a vertebra; such patterns may include three-dimensional (3D) printed patterns, serrated patterns, and other suitable patterns.

The top 210 is substantially rounded rectangular in shape and forms a depressed portion 220 cooperatively defined by the distal end 204, the first lateral side 206, and the second lateral side 208. The depressed portion 220 fully extends to the distal end 204. The depressed portion 220 extends toward the base 106 of the fixed member 100 and is configured to substantially align with the depressed portion 126 of the fixed member 100. The top 210 may have any shape, size, and configuration however. A skilled artisan will be able to determine a suitable top shape, size, and configuration according to a particular example based on various considerations, including the sizes, shapes, and configurations of the transition member and the fixed member. In example embodiments, the top may have any shape, including circular, rectangular, triangular, elliptical, oval, and pentagonal. In other example embodiments, the top may not define the depressed portion. In other example embodiments, the depressed portion may be disposed away from the base, parallel to the base or substantially parallel to the base.

The contacting member 201 and the transition member 230 cooperatively define first and second graft passageways 222, 224. Each of the first and second graft passageways 222, 224 extends from the top 210 to the bottom 212 of the contacting member 201, extends into at least a portion of the transition member 230, and defines a rounded rectangular top opening 223, 225, respectively, on the top 210. The first graft passageway 222 is disposed closer to the proximal end 202 than is the second graft passageway 224. The second graft passageway 224 is partially defined by the depressed portion 220. A skilled artisan will be able to determine suitable first and second graft passageways according to a particular example based on various considerations, including the sizes, shapes, and configurations of the contacting member and the desirability of bone grafting after implantation. In example embodiments, the contacting member may define zero, one, two, three, four, or more than four graft passageways. In example embodiments, the first and second graft passageways may have top openings having any shape, including circular, elliptical, square, rectangular, and triangular. Additionally, the first and second graft passageways may have any diameter.

The lifting member 200 also defines a transition member 230. The transition member 230 includes a proximal end 232, a distal end 234, an outer surface 231, a first lateral side 236, a second lateral side 238, a bottom 239, and first, second, third, and fourth corners 240, 241, 242, 243.

The transition member 230 is adjacent the contacting member 201 such that the distal end 234 is adjacent the distal end 204, the proximal end 232 is adjacent the proximal end 202, the first lateral side 236 is adjacent the first lateral side 206, and the second lateral side 238 is adjacent the second lateral side 208. Additionally, the top (not illustrated in the Figures) of the transition member 230 is adjacent the bottom 212 of the contacting member 201.

The bottom 239 of the transition member 230 is cooperatively formed by each of the proximal end 232, distal end 234, first lateral side 236, and second lateral side 238. The bottom includes each of the first, second, third, and fourth corners 240, 241, 242, 243 (hereinafter, collectively referred to as "the four corners 240, 241, 242, 243") disposed on first, second, third, ad fourth legs (not illustrated in the Figures), respectively. Each of the first and second corners 240, 241 is substantially adjacent a proximal passageway 244 defined by the proximal end 232 of the transition member. The proximal passageway 244 is substantially U-shaped. Each of the third and fourth corners 242, 243 is substantially adjacent a distal passageway 245 that provides access to a cavity 246 that is cooperatively defined by each of the distal end 234, first lateral side 236, second lateral side 238, bottom 239, and top of the transition member 230. Each of the proximal and distal passageways includes a central axis that extends along the respective passageways that is disposed on a plane that is substantially parallel to the plane on which the base of the fixed member is disposed (not illustrated in the Figures). Each of the proximal and distal passageways may have any size, shape, and configuration, and may be defined by any portion of the transition member, however. A skilled artisan will be able to determine suitable proximal and distal passageways according to a particular example based on various considerations, including the desirability of including such a passageways and the size, shape, and configuration of the fixed member. In example embodiments, each of the proximal and distal passageways may have any size, shape, and configuration, including cylindrical, conical, bell-shaped, and box. In example embodiments, the transition member may define only one or neither of the proximal and distal passageways.

The cavity 246 is configured to house the connecting member 250 of the transition member 230. The cavity 246 can house the connecting member 250 when the expandable spinal cage 10 is in the first configuration, the second configuration, and is between transitioned between the two configurations. The cavity 246 is at least partially disposed proximal to the second graft passageway 224 and distal to the first graft passageway 222 relative to the distal end 104 of the fixed member 100. The cavity may have any size, shape, and configuration, and may be defined by any portion of the contacting member, however. A skilled artisan will be able to determine a suitable cavity according to a particular example based on various considerations, including the sizes, shapes, and configurations of the connecting member and the spatial relationship between the contacting member and the fixed member. In example embodiments, the cavity may be disposed nearer the proximal end or distal end of the contacting member, relative to its current position. In example embodiments, the cavity may form one or more windows on any of the first and second lateral sides, top, and distal end of the contacting member and may be in fluid communication with one or more passageways, such as the distal passageway described above.

Each of the four corners 240, 241, 242, 243 is configured to be disposed within the fixed member 100 when the expandable spinal cage is in its first configuration, its second configuration, and when it transitions between the two configurations. This is particularly advantageous because it maintains the stability of the transition member 230 and, therefore, the locking member 200 in its entirety, when one or more vertebrae contact it. By ensuring that each of the four corners 240, 241, 242, 243 remains within the fixed member 100 when the expandable spinal cage 10 is in use, the fixed member 100 can continuously provide stability to the locking member 200 and evenly distribute force amongst the various components of the device, including the driving member 300 and the locking member 400. This prevents the splaying or buckling of the locking member 200 after implantation. Additionally, the locking member 400 adds additional support by interacting with the threaded portion 136 of the fixed member 100 help maintain the positioning of the various components of the expandable spinal cage 10. This configuration allows for the force provided by one or more vertebrae to be transferred to multiple portions of the expandable spinal cage 10, including the fixed member 100 and locking member 400.

The first lateral side 236 defines a passageway (not illustrated in the Figures) extending from its outer surface 231 to its inner surface (not illustrated in the Figures). The second lateral side 238 defines a passageway (not illustrated in the Figures) extending from its outer surface 231 to its inner surface (not illustrated in the Figures). The passageways 236, 238 are substantially cylindrical in shape and configured to at least partially house a pin, described below. Any portion of the contacting member may define the passageways, however. Each of the passageways includes a central axis that extends along the respective passageways that is disposed on a plane that is substantially parallel to the plane on which the base of the fixed member is disposed (not illustrated in the Figures). They may also have any shape, size, and configuration. A skilled artisan will be able to determine how to suitably form the passageways according to a particular example based on various considerations, including the sizes, shapes, and configurations of the pin and lifting member. In example embodiments, the passageways may have any shape, size, and configuration, including pill, pyramid, box, and cone. In example embodiments, the passageways may be defined by any portion of the contacting member, including one or more of the first lateral side, second lateral side, proximal end, distal end, and base.

The transition member 230 includes a first stabilizing mechanism 248 disposed on the outer surface 231 of the first lateral side 236 and a second stabilizing mechanism (not illustrated in the Figures) disposed on the outer surface 231 of the second lateral side 238. Each of the first stabilizing mechanism 248 and second stabilizing mechanism is substantially box-shaped. The first stabilizing mechanism 248 slidably engages a first slot 147 defined by the inner surface 114 of the fixed member 100 and configured to house the first stabilizing mechanism 248. The second stabilizing mechanism slidably engages a second slot 148 defined by the inner surface 114 of the fixed member 100 and configured to house the second stabilizing mechanism. Each of the first stabilizing mechanism 248 and the first slot 147, and the second stabilizing mechanism and the second slot 148 act as a mechanism to prevent a particular movement of the lifting member 200 within the fixed member 100. More specifically, because the first stabilizing mechanism 248 fits snugly within the first slot 147 and the second stabilizing mechanism fits snugly within the second slot 148, excessive movement of the lifting member 200 towards the proximal end 102 or distal end 104 of the fixed member 100 is prevented. A skilled artisan will be able to determine suitable slots and stabilizing mechanisms according to a particular example based on various considerations, including the desirability of including stabilizing mechanisms and the sizes, shapes, and configurations of the fixed member. In example embodiments, the stabilizing mechanisms may have any shape, including pill, pyramid, sphere, cone, cylinder, rectangular, triangular, circular, and semi-circular; they may also have any size and configuration. In example embodiments, the slots may have any shape, including cylindrical, conical, rectangular, beveled, rounded, and dovetailed; they may also have any size and configuration. In example embodiments, any number of stabilizing mechanisms may be included, including zero, one, two, three, four, or more than four. Additionally, the stabilizing mechanisms may be disposed on any portion of the lifting member in other example embodiments.

The connecting member 250 is attached to each of the hinge member 270 and transition member 230 and is at least partially disposed within the fixed member 100. The connecting member 250 may also be at least partially disposed within the cavity 246 of the transition member 230. The connecting member 250 includes a proximal end 252, a distal end 254, a first lateral side 256, and a second lateral side (not illustrated in the Figures). The connecting member 250 includes a first connecting passageway (not illustrated in the Figures) disposed adjacent the proximal end 252 and extending from the first lateral side 256 to the second lateral side and a second connecting passageway (not illustrated in the Figures) disposed adjacent the distal end 254 and extending from the first lateral side 256 to the second lateral side. Each of the first connecting passageway and the second connecting passageway is configured to house a pin, described below. Each of the first connecting passageway and the second connecting passageway is substantially cylindrical in shape. Each of the first and second connecting passageways includes a central axis that extends along the respective passageways that is disposed on a plane that is substantially parallel to the plane on which the base of the fixed member is disposed (not illustrated in the Figures). The first and second connecting passageways may have any sizes, shapes, and configurations, however. A skilled artisan will be able to determine how to suitably form the first and second connecting passageways according to a particular example based on various considerations, including the sizes, shapes, and configurations of the pin and contacting member. In example embodiments, the first and second connecting passageways may have any shape, including pill, pyramid, box, and cone. In example embodiments, the first and second connecting passageways may be defined by any portion of the connecting member, including one or more of the first lateral side, second lateral side, proximal end, and distal end.

The hinge member 270 is disposed within the fixed member 100 and connected to the connecting member 250 and fixed member 100, described below. The hinge member 270 includes a proximal end 272, a distal end 274, a first lateral side 276, and a second lateral side 278. The hinge member 270 includes a first hinge passageway (not illustrated in the Figures) disposed adjacent the proximal end 272 and extending from the outer surface to the inner surface (not illustrated in the Figures) of the first lateral side 276. The hinge member 270 includes a second hinge passageway (not illustrated in the Figures) disposed adjacent the proximal end 272 and extending from the outer surface to the inner surface (not illustrated in the Figures) of the second lateral side 278. The first and second hinge passageways are configured to house a pin, described below. The first and second hinge passageways are substantially cylindrical in shape. Each of the first and second hinge passageways includes a central axis that extends along the respective passageways that is disposed on a plane that is substantially parallel to the plane on which the base of the fixed member is disposed (not illustrated in the Figures). Additionally, the hinge member 270 includes a first fixed extension 280 and a second fixed extension (not illustrated in the Figures)

disposed on the first and second lateral sides 276, 278, respectively. The first 280 and second fixed extensions are configured to be inserted into the first 130 and second pin passageways, respectively, of the fixed member 100. The first 280 and second fixed extensions are substantially cylindrical in shape (and, thus, can be said to be "pin-shaped") and help to provide additional stability to the expandable spinal cage 10. The first and second hinge passageways and first and second fixed extensions may have any sizes, shapes, and configurations, however. A skilled artisan will be able to determine how to suitably form the first and second hinge passageways according to a particular example based on various considerations, including the sizes, shapes, and configurations of the pin and contacting member. In example embodiment, the first and second hinge passageways may have any shape, including pill, pyramid, box, and cone. In example embodiments, the first and second hinge passageways may be defined by any portion of the hinge member, including one or more of the first lateral side, second lateral side, proximal end, and distal end. In example embodiments, the first and second fixed extensions may have any shape, as well, including box, cone, and pyramid.

The driving member 300 is comprised of a first member 310 and a second member 350 and is at least partially disposed within the fixed member 100. The first member 310 is substantially u-shaped and includes a proximal end 312, a distal end 314, a first lateral side 316, a second lateral side 318, first and second wings 320, 322, and a base 326. The proximal end 312 is disposed substantially adjacent the proximal end 102 of the fixed member 100. The first member 310 is also adjacent and in contact with inner surface (not illustrated in the Figures) of the base 106 of the fixed member 100. Additionally, the proximal end 312 is configured to be contacted by the locking member 400, described below. Each of the first and second wings 320, 322 defines a wing passageway 330, 332 extending from the inner surface to the outer surface (not illustrated in the Figures) of each respective wing 320, 322. Each of the wing passageways 330, 332 is configured to house a pin, described below. Each of the wing passageways 330, 332 is substantially cylindrical in shape. Each of the wing passageways 330, 332 includes a central axis that extends along the respective wing passageways 330, 332 that is disposed on a plane (not illustrated in the Figures) that is substantially parallel to the plane (not illustrated in the Figures) on which the base 106 of the fixed member 100 is disposed. The wing passageways may have any sizes, shapes, and configurations, however. A skilled artisan will be able to determine how to suitably form the wing passageways according to a particular example based on various considerations, including the sizes, shapes, and configurations of the pin and contacting member. In example embodiments, the wing passageway may have any shape, including pill, pyramid, box, and cone. In example embodiments, the wing passageways may be defined by any portion of the first member, including one or more of the first lateral side, second lateral side, proximal end, distal end, and base. Additionally, in other example embodiments, the first member may have any size, shape, and configuration and may define no wing passageways.

The second member 350 is elongate and adjacent the base 326 of the first member 310. The second member 350 includes a proximal end 352, a distal end 354, a first lateral side 356, and a second lateral side (not illustrated in the Figures). The distal end 354 of the second member 350 defines a first distal end passageway extending from the outer surface to the inner surface (not illustrated in the Figures) of the first lateral side 356 and a second distal end passageway extending from the outer surface to the inner surface (not illustrated in the Figures) of the second lateral side 358. The second member 350 also defines a proximal end passageway (not illustrated in the Figures) extending from the first lateral side 356 to the second lateral side 358 adjacent the proximal end 352. Each of the first and second distal end and proximal end passageways is configured to house a pin, described below. Each of the first and second distal end and proximal end passageways is substantially cylindrical in shape. Each of the first and second distal end and proximal end passageways includes a central axis that extends along the respective passageways that is disposed on a plane that is substantially parallel to the plane on which the base of the fixed member is disposed (not illustrated in the Figures). The first and second distal end and proximal end passageways may have any size, shape, and configuration, however. A skilled artisan will be able to determine how to suitably form the first and second distal end and proximal end passageways according to a particular example based on various considerations, including the sizes, shapes, and configurations of the pin and contacting member. In example embodiments, the first and second distal end and proximal end passageways may have any shape, including pill, pyramid, box, and cone. In example embodiments, the first and second distal end and proximal end passageways may be defined by any portion of the second member, including one or more of the first lateral side, second lateral side, proximal end, and distal end. Additionally, in other example embodiments, the second member may have any size, shape, and configuration and may define no first and second distal end and/or proximal end passageways.

The distal end 254 of the connecting member 250 is disposed adjacent the first and second lateral sides 236, 238 of the transition member 230. The distal end 254 of the connecting member 250 engages the transition member via a pin, such as pin 499, that extends through each of the distal passageway defined by the connecting member 250, the passageway (not illustrated in the Figures) defined by the first lateral side 236, and the passageway (not illustrated in the Figures) defined by the second lateral side 238. The pin 499 is substantially cylindrical in shape and is configured to be inserted into one or more of the passageways described above. Each of the distal passageway defined by the connecting member 250, the passageway defined by the first lateral side 236, and the passageway defined by the second lateral side 238 is in fluid communication with one another in order to allow the pin 499 to extend through the passageways and, therefore, connect the connecting member 281 to the transition member 201. The connecting member 250 is pivotable about the pin 499. A skilled artisan will be able to determine how to suitably configure the passageways according to a particular example based on various considerations, including the size, shape, and configuration of the pin and the desired mechanism for connecting the members. In example embodiments, the connecting member and the transition member may be integrally formed. In example embodiments, the transition member and the connecting member may be connected by any other physical mechanism or may be connected by an adhesive.

The proximal end 352 of the second member 350 of the locking member is in adjacent the base 324 of the first member 310 and engages a pin, such as pin 498, that extends through each of the first and second passageway defined by the second member 350 and the wing passageways 330, 332 defined by the first and second wings 320, 322. The pin 498 is substantially cylindrical in shape and is configured to be inserted into one or more of the proximal end 352 and wing passageways 330, 332 defined by, respectively, the second member 350 and the first member 300, described above. Each of the wing passageways 330, 332 defined by the first and second wings 320, 322 and the proximal end passageway defined by the first member 350 is in fluid communication with one another in order to allow the pin 498 to extend through the proximal end and wing passageways 330, 332 and, therefore, connect the second member 350 and first member 300. The second member 350 is pivotable about the pin 498 relative to the first member 300. A skilled artisan will be able to determine how to suitably configure the proximal end and wing passageways according to a particular example based on various considerations, including the size, shape, and configuration of the pin and the desired mechanism for connecting the members. In example embodiments, the first member and the second member may be integrally formed. In example embodiments, the first member and the second member may be connected by any other physical mechanism and/or may be connected by one or more adhesives.

The proximal end 252 of the connecting member 250 is disposed adjacent the proximal end 272 of the hinge member 270 and the distal end 354 of the second member 350 of the driving member 300. The connecting member 250 engages a pin, such as pin 497, that extends through each of the second connecting passageway defined by the connecting member 250, the first hinge passageway defined by the hinge member 270, and the first and second distal end passageways defined by the second member 350. The pin 497 is substantially cylindrical in shape and is configured to be inserted into one or more of the first and second distal end, first hinge, and second connecting passageways described above. Each of the second connecting passageway defined by the connecting member 250, the first hinge passageway defined by the hinge member 270, and the first and second distal end passageways defined by the second member 350 is in fluid communication with one another in order to allow the pin 497 to extend through these passageways and, therefore, connect the second member 350, the connecting member 250, and the hinge member 270. The connecting member 250, the second member 350, and hinge member 270 are pivotable about the pin 497. The area adjacent the portion at which the connecting member 250, second member 350, hinge member 270, and pin 497 connect, as described above, comprises a first junction 490. A skilled artisan will be able to determine how to suitably configure the first and second distal end, second connecting, and first hinge passageways according to a particular example based on various considerations, including the size, shape, and configuration of the pin and the desired mechanism for connecting the members. In example embodiments, one or more of the connecting member, the second member, and the hinge member may be integrally formed. In example embodiments, one or more of the connecting member, the second member, and the hinge member may be connected by any other physical mechanism or may be connected by an adhesive.

Figure 8:
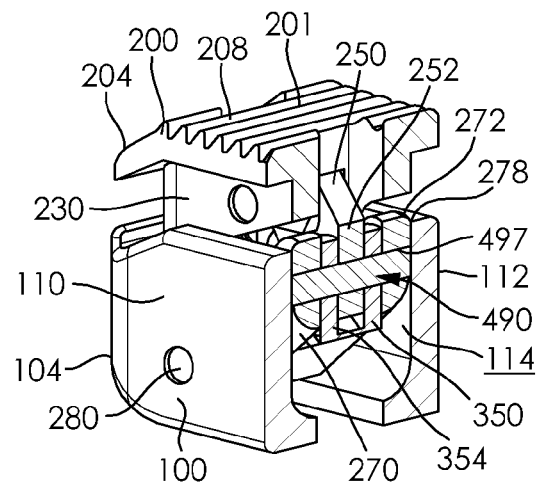
FIG. 8 is a magnified cross-sectional view of the expandable spinal cage illustrated in FIG. 3, taken along line 8-8.
Figure 8A:
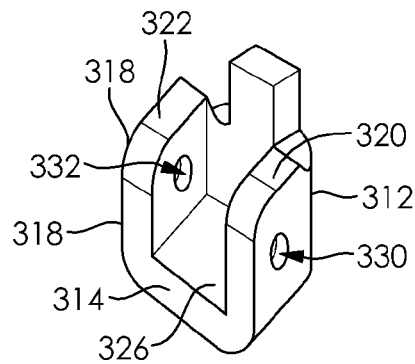
FIG. 8A is a magnified perspective view of the first member of the driving member of the expandable spinal cage illustrated in FIG. 1.

The first junction 490 is best illustrated in FIG. 8. As FIG. 8 illustrates, the first junction 490 is disposed within the fixed member 100 when the expandable spinal cage 10 is in its second configuration. Accordingly, the first junction 490 is housed within the cavity 118 of the fixed member 100 at all times. The components that comprise the first junction 490 are held in place and in contact with one another, in part, due to the force exerted by the inner surface 114 of the fixed member 100. This helps to maintain a solid connection between the various components of the first junction 490. Additionally, it is advantageous to keep the first junction 490 within the cavity 118 and in contact with the inner surface 114 because it is possible that the components of the first junction 490 may buckle or shift without the stability provided by the fixed member 100, should they be raised away from the base 106 in sufficient a manner to substantially reduce the stability provided by the inner surface 114, and, accordingly, the fixed member 100 as a whole. This configuration allows for forces provided by one or more vertebrae to be distributed to multiple portions of the expandable spinal cage 10, including the fixed member 100 and the locking member 400.

The locking member 400 includes a proximal end 402, a distal end 404, an outer surface 406, a threaded portion 408 disposed on the outer surface 406, a recess 410 on the proximal end 402 defined by an inner surface 412, and a set of notches 414. The locking member 400 is configured to be inserted into the locking member passageway 132 and contact the driving member 300 to transition the expandable spinal cage 10 from the first configuration to the second configuration. It is substantially cylindrical in shape. More specifically, the locking member 400 is configured to contact the first member 310 at its proximal end 312. The threaded portion 408 is configured to mate with the threaded portion 136 in order to prevent unwanted movement of the locking member 400 within the locking member passageway 132. Additionally, the set of notches 414 is configured to be engaged by a medical device or other instrument that may manipulate the locking member 400. A skilled artisan will be able to determine a suitable locking member according to a particular example based on various considerations, including the size, shape, and configuration of the locking member passageway of the fixed member and the desired impact with the sliding member. In example embodiments, a pin may be used as an alternative to the locking member. In example embodiments, the locking member may not include one or both of the threaded portions and set of notches. In example embodiments, the locking member may have any shape, including pill, cone, pyramid, and box.

Figure 6:
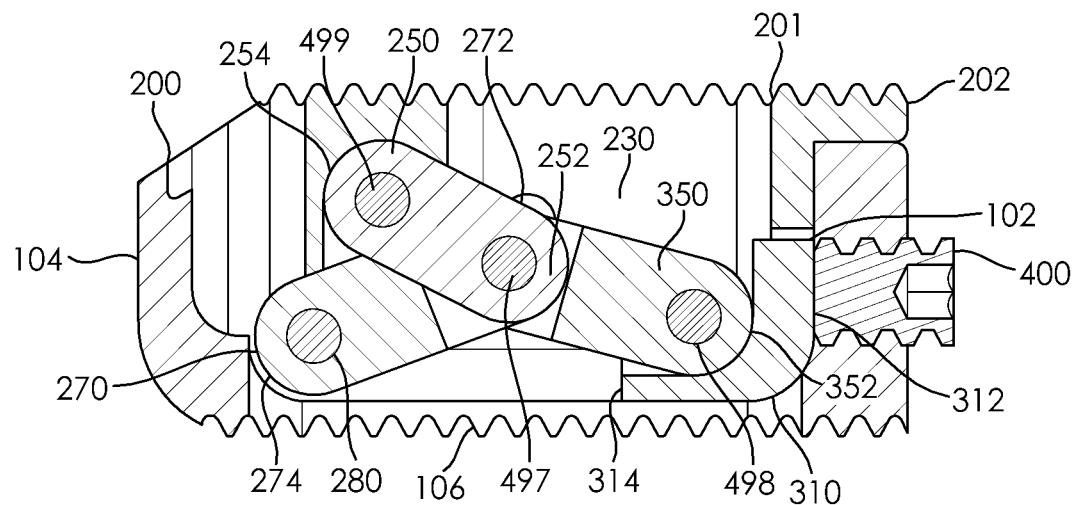
FIG. 6 is a magnified cross-sectional view of the expandable spinal cage illustrated in FIG. 4, taken along line 6-6.
Figure 9:
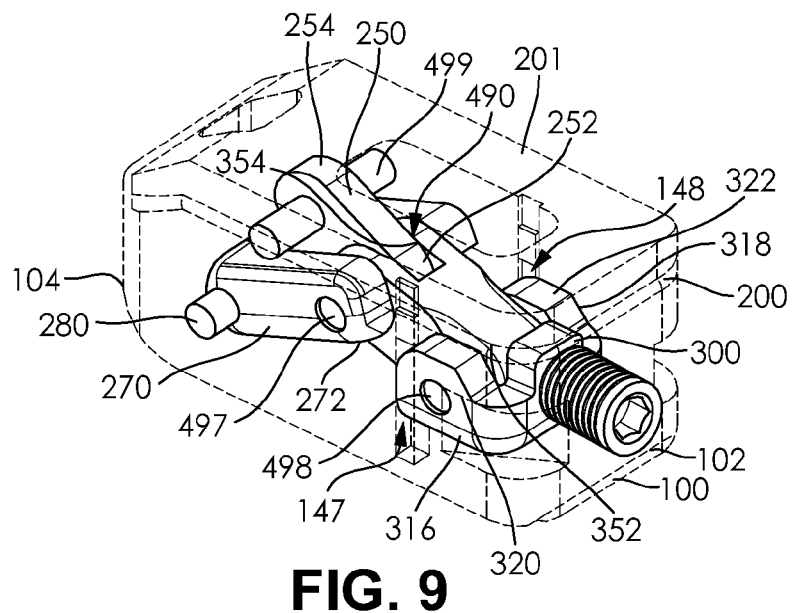
FIG. 9 is a perspective view of the expandable spinal cage illustrated in FIG. 1, with the fixed member, contacting member, and transition member illustrated in phantom.
Figure 10:
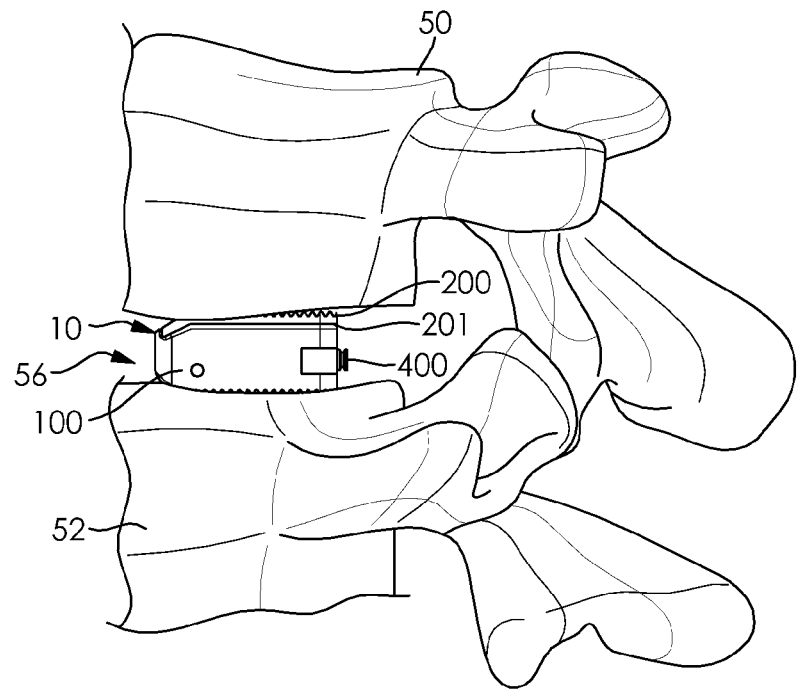
FIG. 10 is a perspective view of two vertebrae from a human vertebral column and the expandable spinal cage illustrated in FIG. 1. The expandable spinal cage is illustrated in a first configuration.
Figure 11:
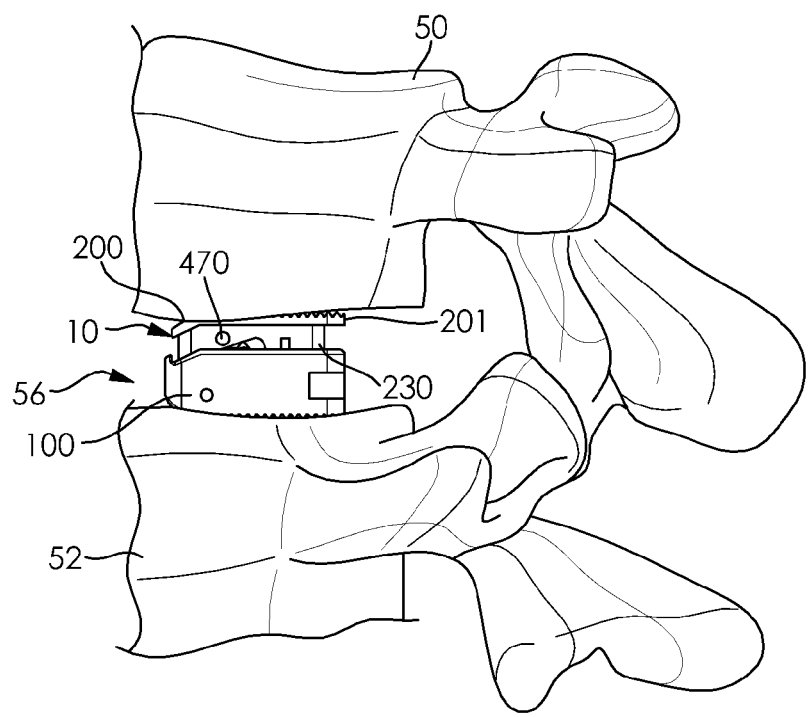
FIG. 11 is a perspective view of two vertebrae from a human vertebral column and the expandable spinal cage illustrated in FIG. 1. The expandable spinal cage is illustrated in a second configuration.

In use, and described in greater detail below, the expandable spinal cage 10 includes first and second configurations. Each of FIGS. 2, 4, 6, 9 and 10 illustrates the expandable spinal cage 10 in the first, contracted configuration. In the first configuration, the contacting member 201 of the lifting member 200 is in contact with and adjacent the perimeter 119 of the fixed member 100. Additionally, the distal end 204 of the contacting member 201 is in contact with and adjacent the ridge 128 of the fixed member 100, keeping them flush against each other when the expandable spinal cage 10 is in the first configuration. As best illustrated in FIG. 6, the first member 310 is substantially adjacent the proximal end 102 of the fixed member 100 and is adjacent, but has not yet been engaged by the locking member 400, which is disposed within the locking member passageway 132 but does not contact the first member 310. As illustrated in FIG. 10, the expandable spinal cage 10 is in contact with two vertebrae 50, 52. More specifically, the top 210 of the contacting member 201 of the lifting member 200 and the lower surface 140 of the base 106 of the fixed member 100 contact the vertebrae 50, 52, respectively.

Figure 7:
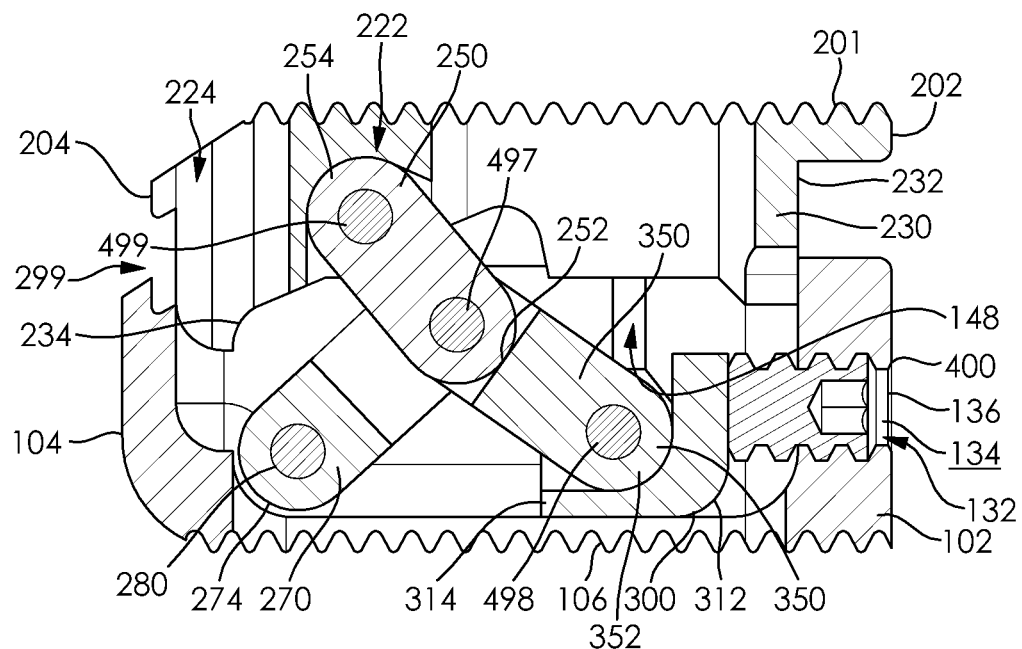
FIG. 7 is a magnified cross-sectional view of the expandable spinal cage illustrated in FIG. 5, taken along line 7-7.

Each of FIGS. 3, 5, 7, 8, and 11 illustrates the expandable spinal cage 10 in the second, expanded configuration. In the second configuration, the contacting member 201 of the lifting member 200 is not in contact with the perimeter 119; the distal end 204 also does not contact the ridge 128. As best illustrated in FIG. 7, the first member 310 has moved toward the distal end 104 of the fixed member 100 along the base 106. This movement occurs because of a force provided by the locking member 400 on the first member 310 of the driving member 300. The first member 310, in turn, provides a force on the second member 350 that causes the second member 350 to pivot away from the base 106. This pivoting movement of the second member 350 causes each of the hinge member 270 and the connecting member 250 to pivot away from the base 106. The connecting member 250, consequently, contacts the transition member 230 and forces it to move away from the base 106. The transition member 230 then contacts the contacting member 201 and forces the contacting member 201 to move away from the base 106. Accordingly, there is a gap 299 disposed between the transition member 230 and the perimeter 119 of the fixed member 100 in this configuration. As illustrated in FIG. 9, the expandable spinal cage 10 is still in contact with two vertebrae 50, 52 when it is in the second configuration; however, the spinal gap 56 between the vertebrae 50, 52 has been altered. In this embodiment, the plane 217 on which the tips 215 of the protruding ridges 213 are disposed is substantially parallel to the plane 146 on which the tips 144 of the protruding ridges 142 of the lower surface 140 of the base 106 are disposed. A skilled artisan will be able to determine how to suitably configure the expandable spinal cage according to a particular example based on various considerations, including the anatomy of the spinal column in which it will be implanted and the desirability of the use of a driving member. In example embodiments, the expandable spinal cage may have one, two, three, or more than three configurations. In example embodiments, the planes may be at obtuse or acute angles relative to one another, or may be parallel to one another. In alternative embodiments, the driving member may be omitted and another mechanical attachment, such as a slider, may be included to transition the device from a first configuration to a second configuration.

Figure 12:
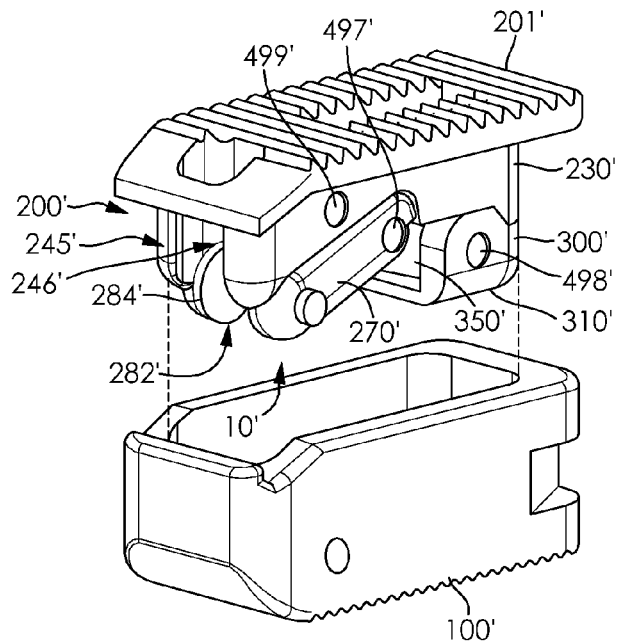
FIG. 12 is a perspective view of an alternative expandable spinal cage.

FIG. 12 illustrates an alternative expandable spinal cage 10'. The expandable spinal cage 10'. The alternative expandable spinal cage 10' is similar to expandable spinal cage 10, except as described below. Thus, the expandable spinal cage 10' comprises a fixed member 100', a lifting member 200' comprising a contacting member 201", a transition member 230', connecting member (not illustrated in the Figures), and a hinge member 270', a driving member 300' comprising a first member 310' and a second member 350', a locking member (not illustrated in the Figures), and pins 497', 498', 499'.

In this alternative embodiment, the distal end 274' of the hinge member 270' defines a slot 282'. The slot 282' is configured such that it may house a disk 284' within the slot 282'. The slot 282' is substantially aligned with the distal passageway 245' and it provides access to the cavity 246' of the transition member 230'. The disk 284' is also partially housed by the cavity 246'. In an example embodiment, the hinge member 270' and disk 284' may be comprised of a flexible material that allows for the disk 284' to easily be placed within the slot 282'. Non-limiting examples of materials considered specifically suitable for use in the various components of the expandable spinal cage 10' include various plastics, Nitinol and other superelastic materials, polyether ether ketone (PEEK) materials, metals, metalloids, and combinations of these materials.

Figure 12A:
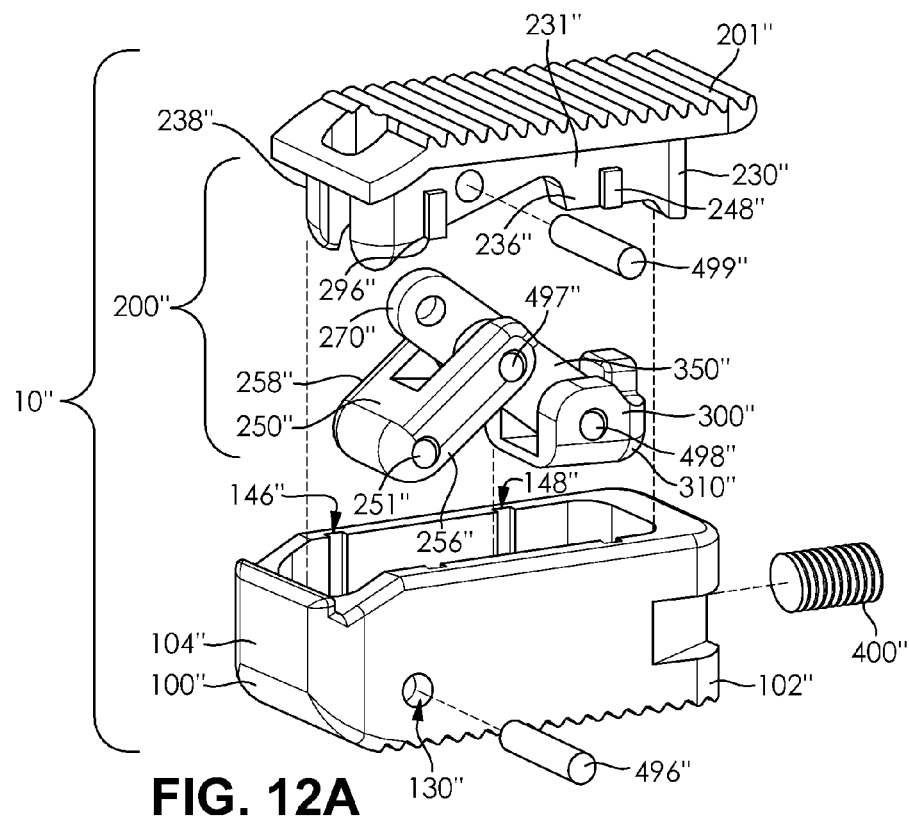
FIG. 12A is an exploded view of an alternative expandable spinal cage.
Figure 12B:
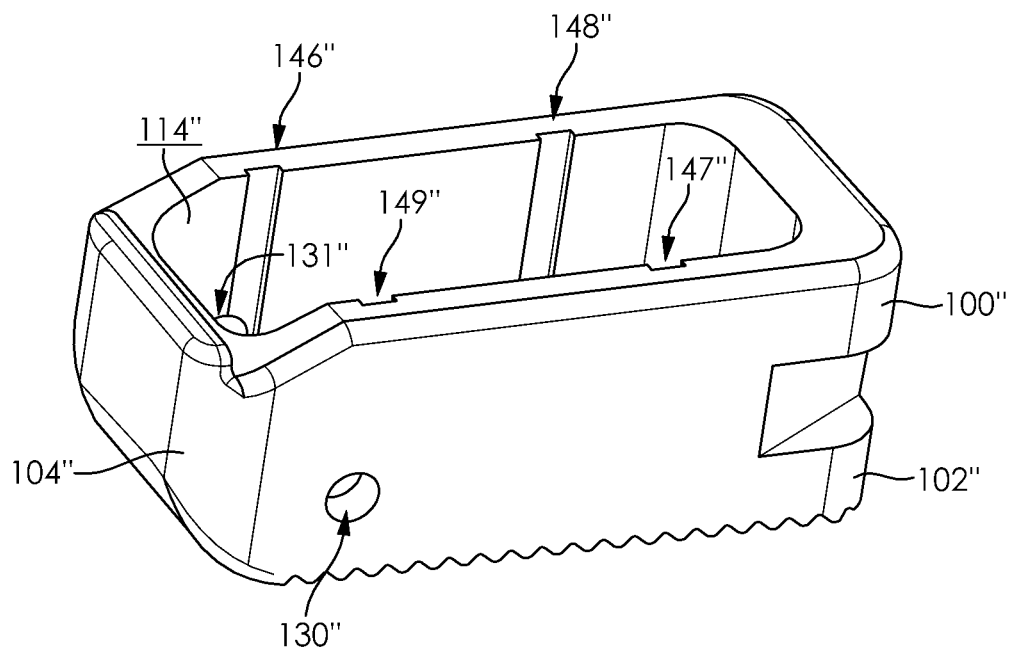
FIG. 12B is a magnified perspective view of a fixed member of the expandable spinal cage illustrated in FIG. 12A.

Each of FIGS. 12A and 12B illustrates an alternative expandable spinal cage 10". The expandable spinal cage 10". The alternative expandable spinal cage 10" is similar to expandable spinal cage 10, except as described below. Thus, the expandable spinal cage 10" comprises a fixed member 100", a lifting member 200" comprising a contacting member 201", a transition member 230", connecting member 250", and a hinge member 270", a driving member 300" comprising a first member 310" and a second member 350", a locking member 400", and pins 497", 498", 499".

In this alternative embodiment, the transition member 230" includes first and third stabilizing mechanisms 248", 296" disposed on the outer surface 231" of the first lateral side 236" and second and fourth stabilizing mechanisms (not illustrated in the Figures) disposed on the outer surface 231" of the second lateral side 238". Each of the first 248", second, third 296", and fourth stabilizing mechanisms is substantially box-shaped. The first stabilizing mechanism 248" slidably engages a first slot 147" defined by the inner surface 114" of the fixed member 100" and configured to house the first stabilizing mechanism 248". The second stabilizing mechanism slidably engages a first slot 148" defined by the inner surface 114" of the fixed member 100" and configured to house the second stabilizing mechanism. The third stabilizing mechanism 296" slidably engages a third slot 149" defined by the inner surface 114" of the fixed member 100" and configured to house the third stabilizing mechanism 296". The fourth stabilizing mechanism slidably engages a first slot 146" defined by the inner surface 114" of the fixed member 100" and configured to house the fourth stabilizing mechanism. Each of the first stabilizing mechanism 248" and the first slot 147", the second stabilizing mechanism and the second slot 148", the third stabilizing mechanism 296" and the third slot 149", and the fourth stabilizing mechanism and the fourth slot 146" act as a mechanism to prevent a particular movement of the lifting member 200" within the fixed member 100". More specifically, because the first 248", second, third 296", and fourth stabilizing mechanisms fit snugly within, respectively, the first, second, third, and fourth slots 147", 148", 149", 146", excessive movement of the lifting member 200" towards the proximal or distal ends 102", 104" of the fixed member 100" is prevented. A skilled artisan will be able to determine suitable slots and stabilizing mechanisms according to a particular example based on various considerations, including the desirability of including stabilizing mechanisms and the sizes, shapes, and configurations of the fixed member. In example embodiments, the stabilizing mechanisms may have any shape, including pill, pyramid, sphere, cone, cylinder, rectangular, triangular, circular, and semi-circular; they may also have any size and configuration. In example embodiments, the slots may have any shape, including cylindrical, conical, rectangular, beveled, rounded, and dovetailed; they may also have any size and configuration. In example embodiments, any number of stabilizing mechanisms may be included, including zero, one, two, three, four, or more than four. Additionally, the stabilizing mechanisms may be disposed on any portion of the lifting member in other example embodiments.

In addition, in this embodiment the connecting member 250" does not include fixed extensions, as described above. Instead, the first and second lateral sides 256", 258" of the connecting member 250" cooperatively define a connecting member passageway 251" extending from the outer surface 255" of the first lateral side 256" to the outer surface (not illustrated in the Figures) of the second lateral side 258". The connecting member passageway 251" is configured to house a pin, such as pin 496". The pin 496" extends through the passageway 251" and the first and second pin passageways 130", 131" of the fixed member 100". The pin 496" helps to maintain the lifting member 200" within the fixed member 100". A skilled artisan will be able to determine how to suitably configure the connecting member according to a particular example based on various considerations, including the desirability of using a pin rather than a fixed extension. In example embodiments, a fixed extension may be used instead of a pin.

Each of FIGS. 13, 14, 15, 16, 17, and 18 illustrates an example expandable spinal cage 20 or one or more components thereof. The illustrated expandable spinal cage 20 is similar to the expandable spinal cage 10 described above and illustrated in FIGS. 1, 2, 3, 4, 5, 6 7, 8, 9, 10, 11, and 12 except as described below. Thus, the expandable spinal cage 20 comprises a fixed member 500, a lifting member 600 comprising a contacting member 601, a transition member 630, a connecting member 650, and a hinge member 670, a driving member 700 comprising a first member 710 and a second member 750, a locking member 800, and pins 897, 898, 899.

The first lateral side 510 of the fixed member 500 defines a first enlarged passageway (not illustrated in the Figures) extending from its outer surface 516 to its inner surface (not illustrated in the Figures). The second lateral side (not illustrated in the Figures) of the fixed member 500 defines a second enlarged passageway (not illustrated in the Figures) extending from its outer surface (not illustrated in the Figures) to its inner surface 514. The first and second enlarged passageways are substantially cylindrical in shape and configured to at least partially house a pin, described below. Any portion of the fixed member 500 may define the first and second enlarged passageways, however. They may also have any sizes, shapes, and configurations. The first and second enlarged passageways are disposed such that they are closer to the contacting member 601 than is the first member 350. A skilled artisan will be able to determine how to suitably form the first and second enlarged passageways according to a particular example based on various considerations, including the sizes, shapes, and configurations of the pin and lifting member. In example embodiments, the first and second enlarged passageways may have any shape, including pill, pyramid, box, and cone. In example embodiments, the first and second enlarged passageways may be defined by any portion of the contacting member, including one or more of the first lateral side, second lateral side, proximal end, distal end, and base.

The first lateral side 636 and second lateral side 638 of the transition member 630 cooperatively define a third enlarged passageway 609 extending from the outer surface (not illustrated in the Figures) of the first lateral side 606 to the outer surface (not illustrated in the Figures) of the second lateral side 608. The third enlarged passageway 609 has a diameter such that when a pin, such as pin 896, is inserted into the third enlarged passageway 609, the third enlarged passageway 609 will be able to engage the pin 896 in at least three configurations. That is to say, the third enlarged passageway 609 and pin 896 do not engage as snugly as do previous passageways and pins described above. The pin 896, however, will still be captive within the expandable spinal cage 20 by the third enlarged passageway 609. The third enlarged passageway 609 is disposed such that is closer the transition member 630 than is the first member 710 of the locking member 700. The third enlarged passageway 609 is substantially cylindrical in shape. Any portion of the transition member may define the third enlarged passageway, however. It may also have any size, shape, and configuration. A skilled artisan will be able to determine how to suitably form the third enlarged passageway according to a particular example based on various considerations, including the sizes, shapes, and configurations of the pin and lifting member. In example embodiments, the third enlarged passageway may have any shape, including pill, pyramid, box, and cone. In example embodiments, the third enlarged passageway may be defined by any portion of the contacting member, including one or more of the first lateral side, second lateral side, proximal end, distal end, and base.

The first and second lateral sides 510, 512 of the fixed member 500 are disposed adjacent the first and second lateral sides 636, 638 of the transition member 630. The fixed member 500 engages the transition member 630 via a pin 896, which extends through each of the third enlarged passageway 609 defined by the transition member 630 and the first and second enlarged passageways defined by the first and second lateral sides 510, 512 of the fixed member 500. Each of the third enlarged passageway 609 defined by the transition member 630 and the first and second enlarged passageways defined by the first and second lateral sides 510, 512 of the fixed member 500 is in fluid communication with one another in order to allow the pin 896 to extend through the passageways and, therefore, connect the fixed member 500 to the transition member 630. The third enlarged passageway 609 allows for the transition member 630 to be pivotable about the pin 896. A skilled artisan will be able to determine how to suitably configure the first, second, and third enlarged passageways according to a particular example based on various considerations, including the sizes, shapes, and configurations of the pin and the desired mechanism for connecting the members. In example embodiments, the fixed member and the transition member may be integrally formed. In example embodiments, the transition member and the fixed member may be connected by any other physical mechanism or may be connected by an adhesive.

Figure 13:
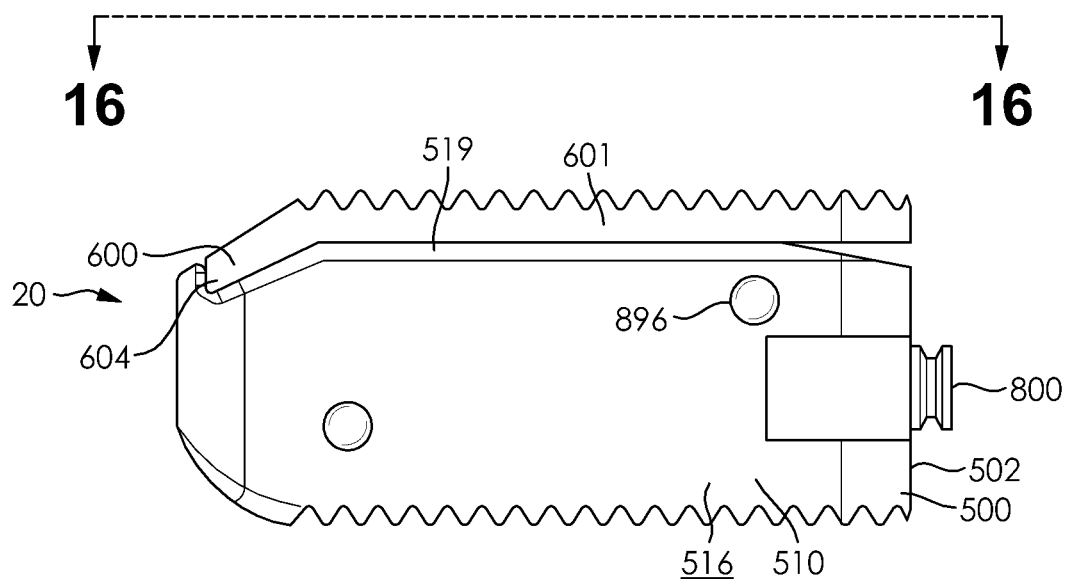
FIG. 13 is a side view of another expandable spinal cage. The expandable spinal cage is illustrated in a first configuration.
Figure 16:
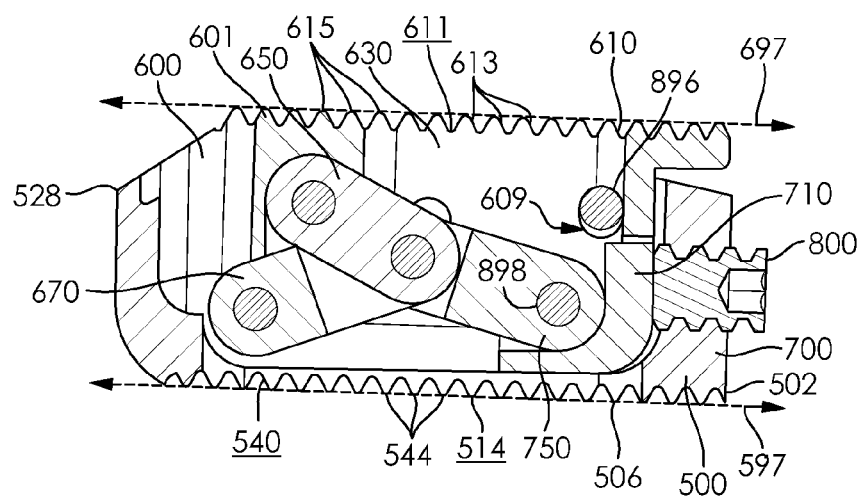
FIG. 16 is a magnified cross-sectional view of the expandable spinal cage illustrated in FIG. 13, taken along line 16-16.

In use, and described in greater detail below, the expandable spinal cage 20 includes first, second, and third configurations. Each of FIGS. 13 and 16 illustrates the expandable spinal cage 20 in the first, contracted configuration. In the first configuration, the contacting member 601 of the lifting member 600 is in contact with and adjacent the perimeter 519 of the fixed member 500. Additionally, the distal end 604 of the contacting member 601 is in contact with and adjacent the ridge 528 of the fixed member 500. As best illustrated in FIG. 16, the first member 710 is substantially adjacent the proximal end 502 of the fixed member 500 and is adjacent, but has not yet been engaged by the locking member 800. Additionally, the plane 697 on which the tips 615 of the set of protruding ridges 613 of the upper surface 611 of the top 610 of the contacting member 601 is disposed is parallel to the plane 597 on which the tips 544 of the set of protruding ridges 542 of the lower surface 540 of the base 506 is disposed when the expandable spinal cage 20 is in the first configuration.

Figure 14:
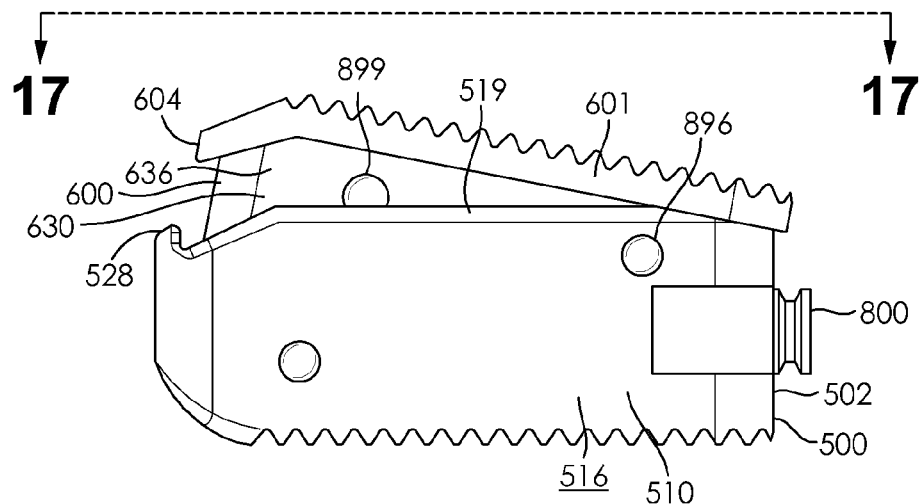
FIG. 14 is a side view of the expandable spinal cage illustrated in FIG. 13. The expandable spinal cage is illustrated in a second configuration.
Figure 17:
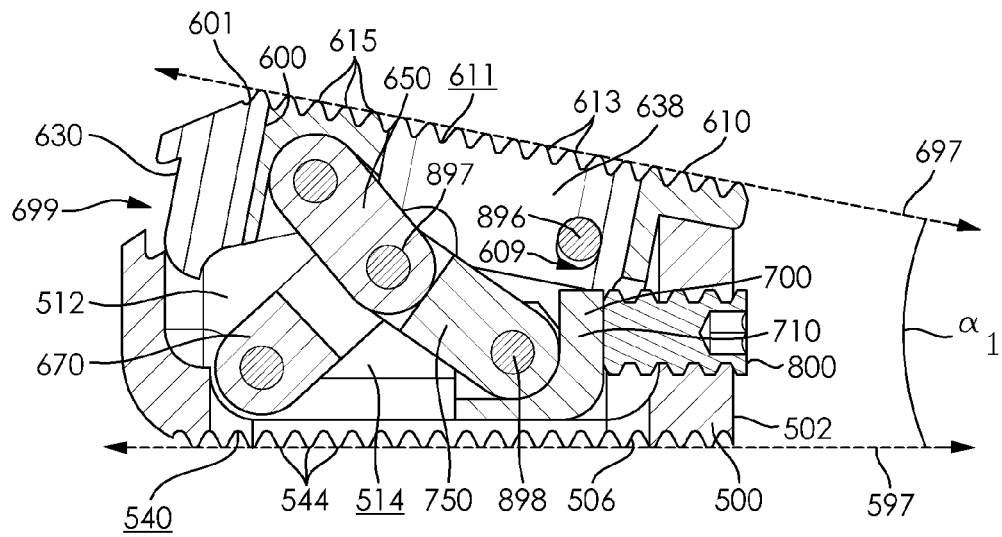
FIG. 17 is a magnified cross-sectional view of the expandable spinal cage illustrated in FIG. 14, taken along line 17-17.

Each of FIGS. 14 and 17 illustrates the expandable spinal cage 20 in the second, intermediate configuration. In the second configuration, the transition member 630 of the lifting member 600 is not in contact with the perimeter 519; the distal end 604 also does not contact the ridge 528. As best illustrated in FIG. 17, the first member 710 of the driving member 700 has moved toward the distal end 504 of the fixed member 500 along the base 506. This movement occurs because of a force provided by the locking member 800 on the first member 710 of the driving member 700. The first member 710, in turn, provides a force on the second member 750 of the driving member 700 that causes the second member 750 to pivot away from the base 506. This pivoting movement of the second member 750 causes each of the hinge member 670 and the connecting member 650 to pivot away from the base 506. The connecting member 650, consequently, contacts the transition member 630 and forces the transition member 630 to move away from the base 506. The contact member 601 also moves away from the base 506 due to the force of the transition member 630. Accordingly, there is a gap 699 disposed between the contacting member 601 and the perimeter 519 of the fixed member 510 when the expandable spinal cage 20 is in the second configuration.

Figure 15:
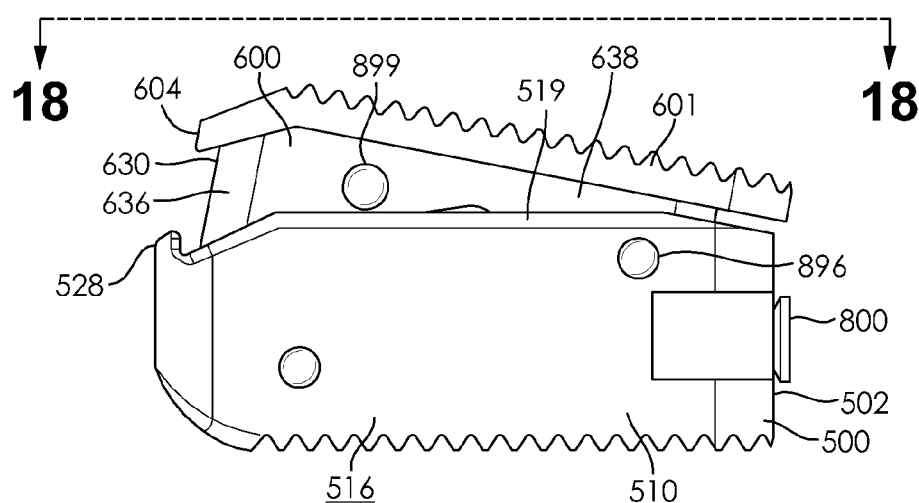
FIG. 15 is a side view of the expandable spinal cage illustrated in FIG. 13. The expandable spinal cage is illustrated in a third configuration.
Figure 18:
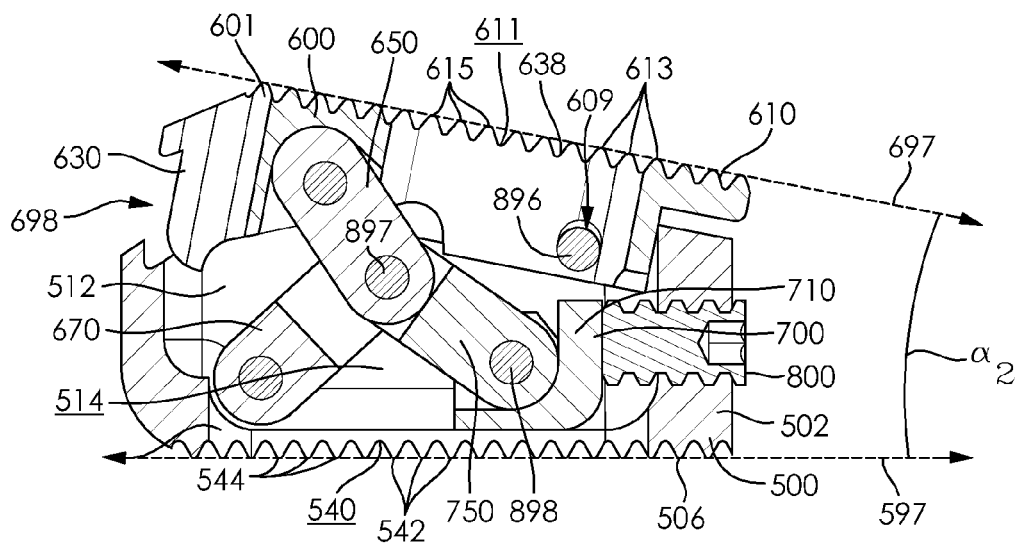
FIG. 18 is a magnified cross-sectional view of the expandable spinal cage illustrated in FIG. 15, taken along line 18-18.

Each of FIGS. 15 and 18 illustrates the expandable spinal cage 20 in the third, expanded configuration. In the third configuration, the transition member 630 of the lifting member 600 is not in contact with the perimeter 519; the distal end 604 also does not contact the ridge 528. As best illustrated in FIG. 17, the first member 710 of the driving member 700 has moved further toward the distal end 504 of the fixed member 500 along the base 506. This movement occurs because of a continued force provided by the locking member 800 on the first member 710 of the driving member 700. The first member 710, in turn, provides a force on the second member 750 of the driving member 700 that causes the second member 750 to pivot away from the base 506. This pivoting movement of the second member 750 causes each of the hinge member 670 and the connecting member 650 to pivot away from the base 506. The connecting member 650, consequently, contacts the transition member 630 and forces the transition member 630 to move away from the base 506. The contact member 601 also moves away from the base 506 due to the force of the transition member 630. Accordingly, there is a larger gap 698 disposed between the contacting member 601 and the perimeter 519 of the fixed member 510 when the expandable spinal cage 20 is in the third configuration than when it is in the second configuration. A skilled artisan will be able to determine how to suitably configure the expandable spinal cage according to a particular example based on various considerations, including the anatomy of the spinal column in which it will be implanted and the desirability of the use of a driving member. In example embodiments, the expandable spinal cage may have one, two, three, or more than three configurations. In example alternative embodiments, the locking member may be omitted and another mechanical attachment, such as a slider, may be included to transition the device from a first configuration to a second configuration.

As discussed above, the third enlarged passageway 609 and first and second enlarged passageways each contains a pin 896. The pin 896 acts to alter the manner in which the lifting member 600 may be expanded as the expandable spinal cage 20 moves from the first configuration to the second configuration. More specifically, as illustrated in FIGS. 16 and 17, the pin 896 is disposed in the uppermost portion (not illustrated in the Figures) of the third enlarged passageway 609 and first and second enlarged passageways when the expandable spinal cage 20 is in the first and second configurations and in the lowermost portion (not illustrated in the Figures) of the third enlarged passageway 609 and first and second enlarged passageways when the expandable spinal cage 20 is in the third configuration. When the expandable spinal cage 20 is transitioned from the first configuration to the second configuration, the pin 896 is not yet manipulated such that it exerts a downward force on the transition member 630. However, when the expandable spinal cage 20 is transitioned from the second configuration to the third configuration, the pin 896 exerts a downward force on the transition member 630. Due to the positioning of the pin 896 within the transition member 630 and fixed member 500, the proximal end 602 of the contacting member 601 is not raised as much as the distal end 604 is when the device is transitioned from the first configuration to the second configuration. Accordingly, the plane 697 on which the tips 615 of the set of protruding ridges 613 of the upper surface 611 of the top 610 is disposed is set at a first angle $\alpha_1$ relative to the plane 597 on which the tips 544 of the set of protruding ridges 542 of the lower surface 540 of the base 506 is disposed when the expandable spinal cage 20 is in the second configuration. Additionally, due to the particular placement of the pin 896 within the transition member 630 and fixed member 500, the proximal end 602 of the contacting member 601 is raised substantially equally as much as the distal end 604 is when the device is transitioned from the second configuration to the third configuration. Accordingly, the plane 697 on which the tips 615 of the set of protruding ridges 613 of the upper surface 611 of the top 610 is disposed is set at a second angle $\alpha_2$ relative to the plane 597 on which the tips 544 of the set of protruding ridges 542 of the lower surface 540 of the base 506 is disposed when the expandable spinal cage 20 is in the second configuration. In various embodiments, the expandable spinal cage may define various first and second angles, however. A skilled artisan will be able to determine a suitable angle according to a particular example based on various considerations, including the anatomy of a vertebral column and the size and shape of the expandable spinal cage. Examples of suitable first angles include angles between about 1° and about 89°, angles between about 30° and about 60°, and angles between about 40° and about 50°. Examples of suitable second angles include angles between about 10° and about 80°, angles between about 30° and about 60°, and angles between about 40° and about 50°. In example embodiments, the planes may be disposed at obtuse or acute angles relative to one another, or may be parallel to one another. In other example embodiments, the proximal end and distal end of the contacting member may move towards or away from the base of the fixed member to any degree; additionally, they may move toward or away from the base of the fixed member at different angles in different configurations, if desired.

Each of FIGS. 19, 20, 21, and 22 illustrates an example expandable spinal cage 30 or one or more components thereof. The illustrated expandable spinal cage 30 is similar to the expandable spinal cage 10 described above and illustrated in FIGS. 1, 2, 3, 4, 5, 6 7, 8, 9, 10, 11, and 12 except as described below. Thus, the expandable spinal cage 30 comprises a fixed member 900, a lifting member 1000 comprising a contacting member 1001, a transition member 1030, a connecting member 1050, and a hinge member 1070, a driving member 1100 comprising a first member 1110 and a second member 1150, a locking member 1200, and pins 1297, 1298, 1299.

The first lateral side 910 of the fixed member 900 defines a first passageway (not illustrated in the Figures) extending from its outer surface 916 to its inner surface (not illustrated in the Figures). The second lateral side (not illustrated in the Figures) of the fixed member 900 defines a second passageway (not illustrated in the Figures) extending from its outer surface (not illustrated in the Figures) to its inner surface 914. The first and second passageways are substantially cylindrical in shape and configured to at least partially house a pin, described below. Any portion of the fixed member 900 may define the first and second passageways, however. They may also have any sizes, shapes, and configurations. The first and second passageways are disposed such that they are closer to the contacting member 1001 than is the first member 1110 of the driving member 1100. A skilled artisan will be able to determine how to suitably form the first and second passageways according to a particular example based on various considerations, including the sizes, shapes, and configurations of the pin and lifting member. In example embodiments, the first and second passageways may have any shape, including pill, pyramid, box, and cone. In example embodiments, any portion of the contacting member, including one or more of the first lateral side, second lateral side, proximal end, distal end, and base, may define the first and second passageways.

The first lateral side 1036 and second lateral side (not illustrated in the Figures) of the transition member 1030 cooperatively define a third passageway (not illustrated in the Figures) extending from the outer surface (not illustrated in the Figures) of the first lateral side 1036 to the outer surface (not illustrated in the Figures) of the second lateral side. The third passageway has a diameter such that when a pin, such as pin 1296, is inserted into the third passageway, the third passageway will be able to snugly engage the pin 1296 in at least three configurations. The pin 1296 is captive within the expandable spinal cage 30 by the third passageway. The third passageway is disposed such that is closer the transition member 1030 than is the first member 1110 of the driving member 1100. The third passageway is substantially cylindrical in shape. Any portion of the transition member may define the third passageway, however. It may also have any size, shape, and configuration. A skilled artisan will be able to determine how to suitably form the third passageway according to a particular example based on various considerations, including the sizes, shapes, and configurations of the pin and lifting member. In example embodiments, the third passageway may have any shape, including pill, pyramid, box, and cone. In example embodiments, any portion of the contacting member, including one or more of the first lateral side, second lateral side, proximal end, distal end, and base, may define the third passageway.

The first 910 and second lateral sides of the fixed member 900 are disposed adjacent the first 1036 and second lateral sides of the transition member 1030. The fixed member 900 engages the transition member 1030 via a pin 1296, which extends through each of the third passageway defined by the transition member 1030 and the first and second passageways defined by the first 910 and second lateral sides of the fixed member 900. Each of the third passageway defined by the transition member 1030 and the first and second passageways defined by the first 910 and second lateral sides of the fixed member 900 is in fluid communication with one another in order to allow the pin 1296 to extend through the passageways and, therefore, connect the fixed member 900 to the transition member 1030. The third passageway allows for the transition member 1030 to be pivotable about the pin 1296. A skilled artisan will be able to determine how to suitably configure the first, second, and third passageways according to a particular example based on various considerations, including the sizes, shapes, and configurations of the pin and the desired mechanism for connecting the members. In example embodiments, the fixed member and the transition member may be integrally formed. In example embodiments, the transition member and the fixed member may be connected by any other physical mechanism or may be connected by an adhesive.

Figure 19:
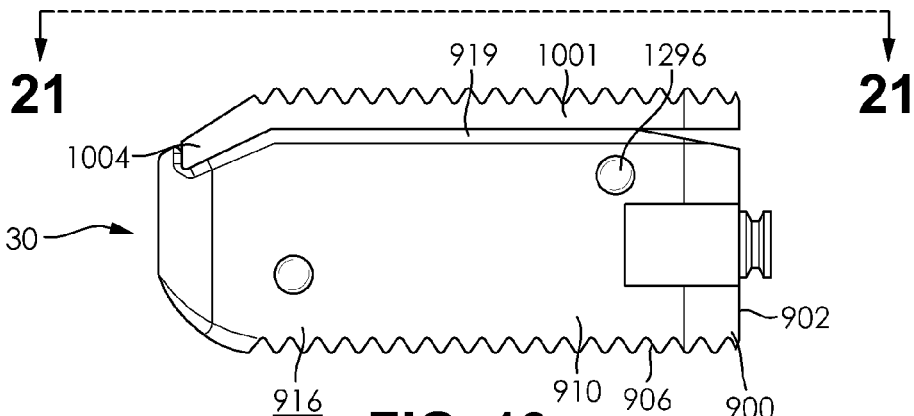
FIG. 19 is a side view of another expandable spinal cage. The expandable spinal cage is illustrated in a first configuration.
Figure 21:
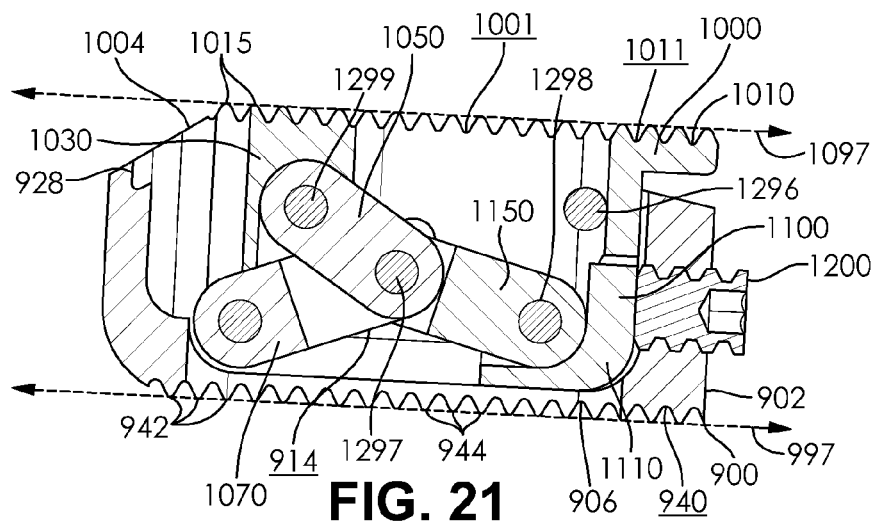
FIG. 21 is a magnified cross-sectional view of the expandable spinal cage illustrated in FIG. 19, taken along line 21-21.

In use, and described in greater detail below, the expandable spinal cage 30 includes first and second configurations. Each of FIGS. 19 and 21 illustrates the expandable spinal cage 30 in the first, contracted configuration. In the first configuration, the contacting member 1001 of the lifting member 1000 is in contact with and adjacent the perimeter 919 of the fixed member 900. Additionally, the distal end 1004 of the contacting member 1001 is in contact with and adjacent the ridge 928 of the fixed member 900. As best illustrated in FIG. 21, the first member 1010 is substantially adjacent the proximal end 902 of the fixed member 900 and is adjacent, but has not yet been engaged by, the locking member 1200. Additionally, the plane 1097 on which the tips 1015 of the set of protruding ridges 1013 of the upper surface 1011 of the top 1010 of the contacting member 1001 is disposed is parallel to the plane 997 on which the tips 944 of the set of protruding ridges 942 of the lower surface 940 of the base 906 is disposed when the expandable spinal cage 30 is in the first configuration.

Figure 20:
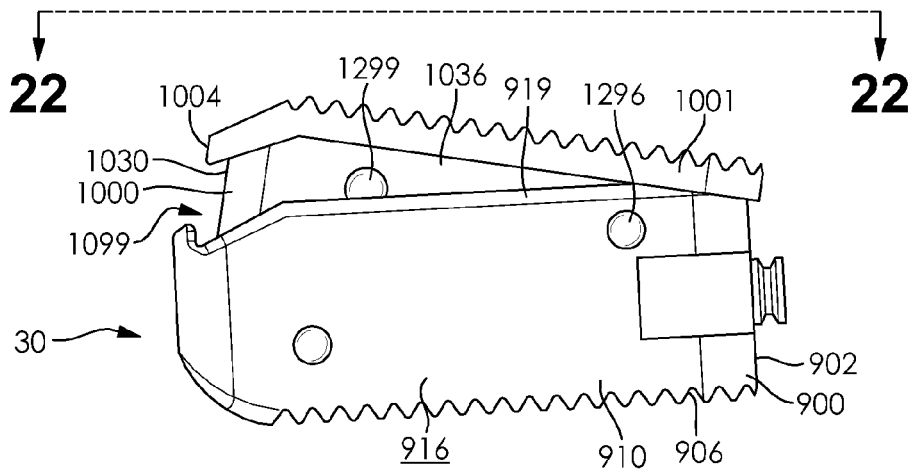
FIG. 20 is a side view of the expandable spinal cage illustrated in FIG. 19. The expandable spinal cage is illustrated in a second configuration.
Figure 22:
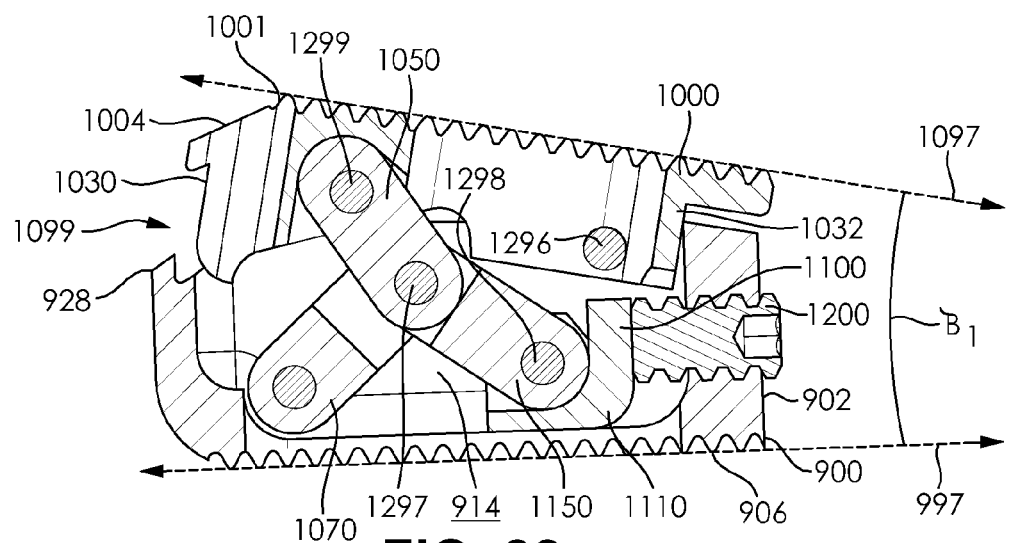
FIG. 22 is a magnified cross-sectional view of the expandable spinal cage illustrated in FIG. 20, taken along line 22-22.

Each of FIGS. 20 and 22 illustrates the expandable spinal cage 30 in the second, expanded configuration. In the second configuration, the transition member 1030 of the lifting member 1000 is not in contact with the perimeter 919; the distal end 1004 also does not contact the ridge 928. As best illustrated in FIG. 22, the first member 1110 of the driving member 1100 has moved toward the distal end 904 of the fixed member 900 along the base 906. This movement occurs because of a force provided by the locking member 1200 on the first member 1110 of the driving member 1100. The first member 1110, in turn, provides a force on the second member 1150 of the driving member 1100 that causes the second member 1150 to pivot away from the base 906. This pivoting movement of the second member 1150 causes each of the hinge member 1070 and the connecting member 1050 to pivot away from the base 1006. The connecting member 1050, consequently, contacts the transition member 1030 and forces the transition member 1030 to move away from the base 906. The contact member 1001 also moves away from the base 906 due to the force of the transition member 1030. Accordingly, there is a gap 1099 disposed between the contacting member 1001 and the perimeter 919 of the fixed member 900 when the expandable spinal cage 30 is in the second configuration. A skilled artisan will be able to determine how to suitably configure the expandable spinal cage according to a particular example based on various considerations, including the anatomy of the spinal column in which it will be implanted and the desirability of the use of a driving member. In example embodiments, the expandable spinal cage may have one, two, three, or more than three configurations. In example alternative embodiments, the locking member may be omitted and another mechanical attachment, such as a slider, may be included to transition the device from a first configuration to a second configuration.

As described above, the third passageway and first and second passageways each contains a pin 1296. The pin 1296 acts to alter the manner in which the lifting member 1000 may be expanded as the expandable spinal cage 30 moves from the first configuration to the second configuration. More specifically, as illustrated in FIGS. 21 and 22, the pin 1296 is disposed in the third passageway and first and second passageways when the expandable spinal cage 30 is in the first and second configurations. When the expandable spinal cage 30 is transitioned from the first configuration to the second configuration, the pin 1296 exerts a downward force on the proximal end 1032 of the transition member 1030. Due to the positioning of the pin 1296 within the transition member 1030 and fixed member 900, the proximal end 1002 of the contacting member 1001 is not raised as much as the distal end 1004 is when the device is transitioned from the first configuration to the second configuration. Accordingly, the plane 1097 on which the tips 1015 of the set of protruding ridges 1013 of the upper surface 1011 of the top 1010 is disposed is set at a first angle $\beta_1$ relative to the plane 1097 on which the tips 944 of the set of protruding ridges 942 of the lower surface 940 of the base 906 is disposed when the expandable spinal cage 30 is in the second configuration. In various embodiments, the expandable spinal cage may define various first angles, however. A skilled artisan will be able to determine a suitable angle according to a particular example based on various considerations, including the anatomy of a vertebral column and the size and shape of the expandable spinal cage. Examples of suitable first angles include angles between about 1° and about 89°, angles between about 30° and about 60°, and angles between about 40° and about 50°. In example embodiments, the planes may be disposed at obtuse or acute angles relative to one another, or may be parallel to one another. In other example embodiments, the proximal end and distal end of the contacting member may move towards or away from the base of the fixed member to any degree; additionally, they may move toward or away from the base of the fixed member at different angles in different configurations, if desired.

Figure 23:
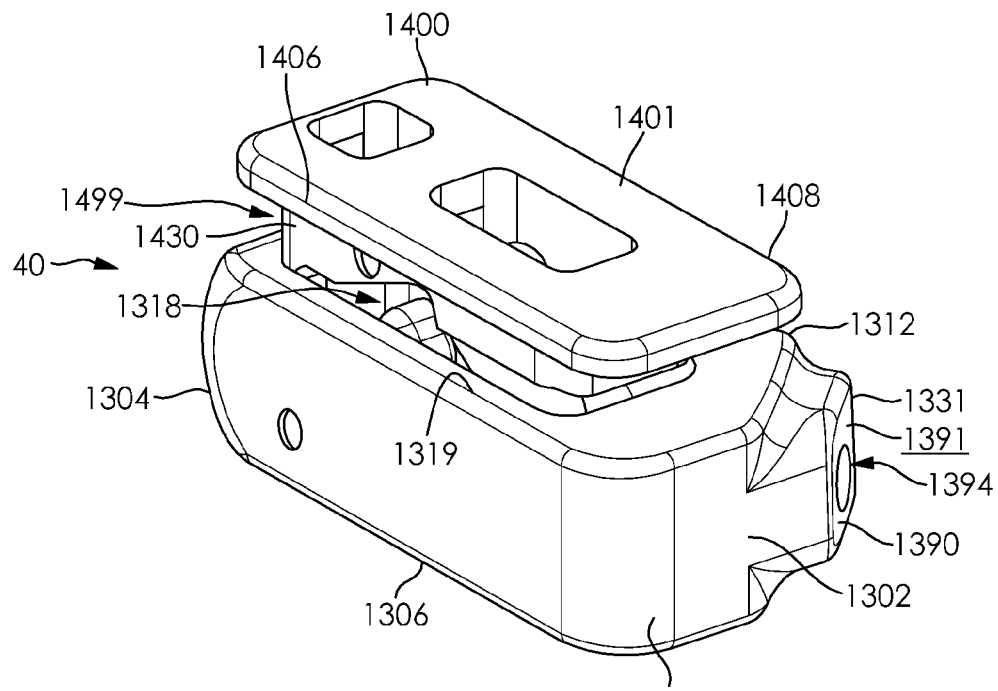
FIG. 23 is a perspective view of another example expandable spinal cage.
Figure 24:
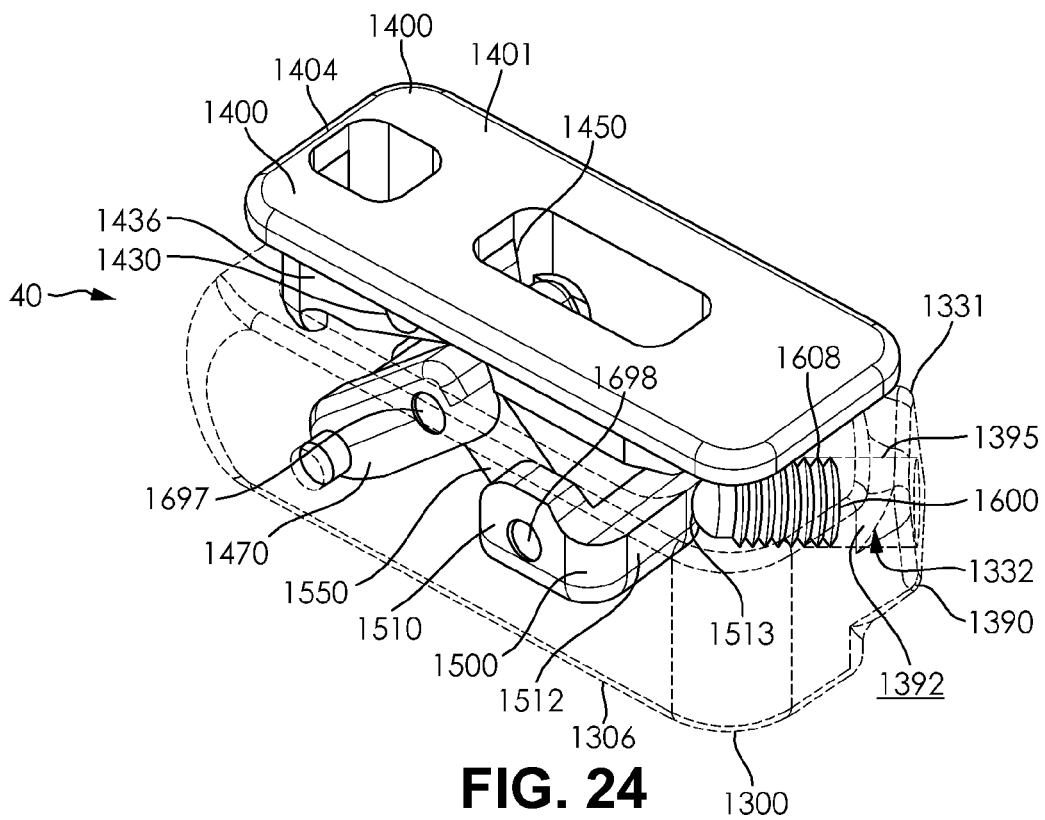
FIG. 24 is a perspective view of the expandable spinal cage illustrated in FIG. 23, with the fixed member illustrated in phantom.

Each of FIGS. 23 and 24 illustrates an example expandable spinal cage 40 or one or more components thereof. The illustrated expandable spinal cage 40 is similar to the expandable spinal cage 10 described above and illustrated in FIGS. 1, 2, 3, 4, 5, 6 7, 8, 9, 10, 11, and 12 except as described below. Thus, the expandable spinal cage 40 comprises a fixed member 1300, a lifting member 1400 comprising a contacting member 1401, a transition member 1430, a connecting member 1450, and a hinge member 1470, a driving member 1500 comprising a first member 1510 and a second member 1550, a locking member 1600, and pins 1697, 1698.

In the illustrated embodiment, the fixed member 1300 defines a locking member passageway 1332 at a first corner 1331 at which the proximal end 1302 is adjacent the second lateral side 1312. Additionally, the proximal end 1302 and second lateral side 1312 cooperatively form a protrusion 1390. The protrusion 1390 extends away from the cavity 1318 of the fixed member 1300 and defines an outer surface 1391 and an inner surface 1392. The outer surface 1391 is substantially rectangular in shape and defines an opening 1394 to the locking member passageway 1332 that is cooperatively defined by the outer surface 1391 and the inner surface 1392. The locking member passageway 1332 is configured to engage and house the locking member 1600 and includes a threaded portion 1395 defined by the inner surface 1392. The threaded portion 1395 of the locking member passageway 1332 engages the threaded portion 1608 of the locking member 1600.

In use, and described in greater detail below, the expandable spinal cage 40 includes first and second configurations. When the expandable spinal cage 40 is in the first configuration (not illustrated in the Figures), the contacting member 1401 of the lifting member 1400 is in contact with and adjacent the perimeter 1319 of the fixed member 1300. Additionally, the distal end 1404 of the contacting member 1401 is in contact with and adjacent the distal end 1304 of the fixed member 1300. The locking member 1600 is disposed within the locking member passageway 1332, but does not yet contact the first member 1510 of the driving member 1500 in this configuration.

Each of FIGS. 23 and 24 illustrates the expandable spinal cage 40 in a second, expanded configuration. In the second configuration, the contacting member 1401 of the lifting member 1400 has been displaced away from and is not in contact with the perimeter 1319 of the fixed member 1300. As best illustrated in FIG. 24, the first member 1510 of the driving member 1500 has moved toward the distal end 1304 of the fixed member 1300 along the base 1306, relative to its position when in the first configuration. This movement occurs because of a force provided by the locking member 1600 on the first member 1510 of the driving member 1500. The first member 1510, in turn, provides a force on the second member 1550 that causes the second member 1550 to pivot away from the base 1306. This pivoting movement of the second member 1550 causes each of the hinge member 1470 and the connecting member 1450 to pivot away from the base 1306, as well. The transition member 1430 then contacts the contacting member 1401 and forces it to move away from the base 1306. Accordingly, gap 1499 is formed between the transition member 1430 and the perimeter 1319 of the fixed member 1300 in this configuration.

In this embodiment, the locking member 1600 provides a force on the proximal end 1512 of the first member 1510 of the driving member 1500. More specifically, the locking member 1600 provides force on the first corner 1513 of the first member 1510, which is disposed adjacent each of the proximal end 1512 and the second lateral side (not illustrated in the Figures). Due to the force being placed on the first corner 1513, rather than directly on the proximal end 1512, as is described in embodiments above, the first lateral side 1436 and second lateral side (not illustrated in the Figures) of the transition member 1430 are raised away from the base 1306 to different degrees. More specifically, the first lateral side 1436 is raised away from the base 1306 to a greater degree than is the second lateral side. The first lateral side 1406 of the contacting member 1401, therefore, is raised away from the base 1306 to a greater degree than is the second lateral side 1408 of the contacting member 1408. Accordingly, the first lateral side 1406 is closer to the perimeter 1319 than is the second lateral side 1408 when the expandable spinal cage 40 is in the second configuration. A skilled artisan will be able to determine how to suitably configure the expandable spinal cage according to a particular example based on various considerations, including the anatomy of the spinal column in which it will be implanted and the desirability of the use of a driving member. In example embodiments, the expandable spinal cage may have one, two, three, or more than three configurations. In example embodiments, the any portion of the transition member may be raised away from the base to any degree; for example, the second lateral side of the transition member may be raised away from the base to a greater degree than is the first lateral side, in another embodiment. In alternative embodiments, the driving member may be omitted and another mechanical attachment, such as a slider, may be included to transition the device from a first configuration to a second configuration.

All components of the expandable spinal cages can be made from any suitable material. Non-limiting examples of suitable materials include metals, such as stainless steel, titanium, cobalt-chromium, and other metals, and plastics commonly used in medical devices. Non-limiting examples of materials considered specifically suitable for use in the expandable spinal cages include Nitinol and other superelastic materials, polyurethane materials, silicone materials, and polyether ether ketone (PEEK) materials.

Those with ordinary skill in the art will appreciate that various modifications and alternatives for the described and illustrated embodiments can be developed in light of the overall teachings of the disclosure. Accordingly, the particular arrangements disclosed are intended to be illustrative only and not limiting as to the scope of the invention, which is to be given the full breadth of the appended claims and any and all equivalents thereof.

We claim:

1. An expandable spinal cage having a first configuration and a second configuration and configured to engage a vertebra, comprising:
   a fixed member having a proximal end, a distal end, a base, an open end substantially opposite the base, an inner surface, and an outer surface, the base, the open end, and the inner surface cooperatively defining a cavity, the inner surface and the outer surface cooperatively defining a passageway on the proximal end in fluid communication with the cavity;
   a lifting member partially disposed within the cavity of the fixed member and comprising a contacting member and a transition member, the contacting member having a lower surface and an upper surface configured to contact the vertebra, the contacting member being disposed adjacent the open end, the transition member in contact with the lower surface;
   a driving member disposed within the cavity of the fixed member and configured to exert force on the lifting member; and
   a locking member configured to be inserted into the passageway and contact the driving member to transition the expandable spinal cage from the first configuration to the second configuration, the locking member moveable axially within the passageway resulting in axial movement of a portion of the driving member;
   wherein the upper surface is disposed further from the base when the expandable spinal cage is in the second configuration than when the expandable spinal cage is in the first configuration.

2. The expandable spinal cage of claim 1, wherein the upper surface is disposed on a plane that is substantially parallel to a plane on which the base is disposed when the expandable spinal cage is in the second configuration.

3. The expandable spinal cage of claim 1, wherein the distal end of the fixed member defines a ridge; and
   wherein a distal end of the contacting member is in contact with the ridge such that the distal end of the contacting member is flush against the ridge.

4. The expandable spinal cage of claim 1, wherein the driving member comprises a first member and a second member.

5. The expandable spinal cage of claim 1, further comprising a hinge member having a proximal end and a distal end, the proximal end fully disposed within the cavity of the fixed member.

6. The expandable spinal cage of claim 5, wherein the hinge member defines first and second fixed extensions;
   wherein the first fixed extension is configured to be inserted into a first fixed extension passageway defined by the fixed member; and
   wherein the second fixed extension is configured to be inserted into a second fixed extension passageway defined by the fixed member.

7. The expandable spinal cage of claim 1, wherein the lifting member comprises a connecting member having a proximal end and a distal end;
   wherein the transition member includes a bottom that defines a transition member cavity; and
   wherein the distal end of the connecting member is disposed within the transition member cavity.

8. The expandable spinal cage of claim 1, wherein the passageway defines a thread.

9. The expandable spinal cage of claim 8, wherein the locking member defines an outer surface having a thread that is configured to mate with the thread defined by the passageway.

10. The expandable spinal cage of claim 1, wherein the upper surface defines a set of protruding ridges configured to engage a vertebra.

11. The expandable spinal cage of claim 1, wherein the fixed member comprises a first lateral side having a first lateral side inner surface and a second lateral side having a second lateral side inner surface;
    wherein the first lateral side inner surface defines a first slot;
    wherein the second lateral side inner surface defines a second slot;
    wherein the first lateral side inner surface defines a third slot; and
    wherein the second lateral side inner surface defines a fourth slot.

12. An expandable spinal cage having a first configuration and a second configuration and configured to engage a vertebra, comprising:
    a fixed member having a proximal end, a distal end, a base, an open end substantially opposite the base, an inner surface, and an outer surface, the base, the open end, and the inner surface cooperatively defining a cavity, the inner surface and the outer surface cooperatively defining a passageway on the proximal end in fluid communication with the cavity;
    a lifting member partially disposed within the cavity of the fixed member and comprising a contacting member and a transition member, the contacting member having a lower surface and an upper surface configured to contact the vertebra, the contacting member being disposed adjacent the open end, the transition member in contact with the lower surface;
    a driving member disposed within the cavity of the fixed member and configured to exert force on the lifting member; and
    a locking member configured to be inserted into the passageway and contact the driving member to transition the expandable spinal cage from the first configuration to the second configuration;
    wherein the upper surface is disposed further from the base when the expandable spinal cage is in the second configuration than when the expandable spinal cage is in the first configuration;
    wherein the fixed member comprises a first lateral side having a first lateral inner surface and a second lateral side having a second lateral inner surface;
    wherein the first lateral side inner surface defines a first slot;
    wherein the second lateral side inner surface defines a second slot;
    wherein the first lateral side inner surface defines a third slot;
    wherein the second lateral side inner surface defines a fourth slot; and
    wherein the transition member defines a first stabilizing mechanism configured to engage the first slot.

13. The expandable spinal cage of claim 12, wherein the transition member defines a second stabilizing mechanism configured to engage the second slot.

14. The expandable spinal cage of claim 13, wherein the transition member defines a third stabilizing mechanism configured to engage the third slot.

15. The expandable spinal cage of claim 14, wherein the transition member defines a fourth stabilizing mechanism configured to engage the fourth slot.

16. An expandable spinal cage having a first configuration and a second configuration and configured to engage a vertebra, comprising:

- a fixed member having a proximal end, a distal end, a first lateral side, a second lateral side substantially opposite the first lateral side, a base, and an open end substantially opposite the base, the base, an inner surface, and an outer surface, the open end, and the inner surface cooperatively defining a cavity, the inner surface and the outer surface cooperatively defining a first passageway on the proximal end in fluid communication with the cavity, the first lateral side defining an inner surface and an outer surface, the second lateral side defining an inner surface and an outer surface, the first lateral side inner surface defining a first slot, the second lateral side inner surface defining a second slot, the fixed member defining a second passageway extending from the inner surface of the first lateral side to the outer surface of the first lateral side, and a third passageway extending from the inner surface of the second lateral side to the outer surface of the second lateral side;
- a lifting member partially disposed within the cavity of the fixed member and comprising a contacting member and a transition member, the contacting member having a lower surface and an upper surface configured to contact the vertebra, the contacting member being disposed adjacent the open end, the transition member in contact with the lower surface, the transition member defining a first stabilizing mechanism configured to engage the first slot, the transition member defining a second stabilizing mechanism configured to engage the second slot;
- a driving member disposed within the cavity of the fixed member and configured to exert force on the lifting member; and
- a locking member configured to be inserted into the first passageway and contact the driving member to transition the expandable spinal cage from the first configuration to the second configuration, the locking member moveable axially within the passageway resulting in axial movement of a portion of the driving member;
- wherein the upper surface is disposed further from the base when the expandable spinal cage is in the second configuration than when the expandable spinal cage is in the first configuration.

17. The expandable spinal cage of claim 16, wherein the transition member defines a first lateral side having an outer surface and a second lateral side having an outer surface; and
   wherein the first lateral side and second lateral side of the transition member cooperatively define an enlarged passageway extending from the outer surface of the first lateral side to the outer surface of the second lateral side.

18. The expandable spinal cage of claim 17, wherein the enlarged passageway is configured to allow a pin to be inserted into the enlarged passageway; and
   wherein an inner surface of the enlarged passageway is configured to engage the pin.

19. The expandable spinal cage of claim 16, wherein the upper surface is disposed on a plane that is set at a first, non-orthogonal angle to a plane on which the base is disposed when the expandable spinal cage is in the second configuration.

20. An expandable spinal cage having a first configuration and a second configuration and configured to engage a vertebra, comprising:

- a fixed member having a proximal end, a distal end, a first lateral side, a second lateral side substantially opposite the first lateral side, a base, an open end substantially opposite the base, an inner surface, and an outer surface, the base, the open end, and the inner surface cooperatively defining a cavity, the inner surface and the outer surface cooperatively defining a passageway on the proximal end in fluid communication with the cavity, the first lateral side defining a first lateral side inner surface, the second lateral side defining a second lateral side inner surface, the first lateral side inner surface defining a first slot, the second lateral side inner surface defining a second slot;
- a lifting member partially disposed within the cavity of the fixed member and comprising a contacting member, a transition member, a connecting member, and a hinge member, the contacting member having a lower surface and an upper surface configured to contact the vertebra, the contacting member being disposed adjacent the open end, the transition member in contact with the lower surface, the transition member defining a first stabilizing mechanism configured to engage the first slot, the transition member defining a second stabilizing mechanism configured to engage the second slot;
- a driving member disposed within the cavity of the fixed member and configured to exert force on the lifting member; and
- a locking member configured to be inserted into the passageway and contact the driving member to transition the expandable spinal cage from the first configuration to the second configuration, the locking member moveable axially within the passageway resulting in axial movement of a portion of the driving member;
- wherein the upper surface is disposed further from the base when the expandable spinal cage is in the second configuration than when the expandable spinal cage is in the first configuration;
- wherein the upper surface is disposed on a plane that is set at a first, non-orthogonal angle to a plane on which the base is disposed when the expandable spinal cage is in the second configuration; and
- wherein the first, non-orthogonal angle is between about 1° and about 30°.

* * * * *